US008642824B2

(12) United States Patent  (10) Patent No.: US 8,642,824 B2
Lemke et al.  (45) Date of Patent: Feb. 4, 2014

(54) CHEMICAL METHODS FOR TREATING A METATHESIS FEEDSTOCK

(75) Inventors: Daniel W. Lemke, Cokato, MN (US);
Kevin D. Uptain, Edina, MN (US);
Francis Amore, Plymouth, MN (US);
Tim Abraham, Minnetonka, MN (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 500 days.

(21) Appl. No.: 12/672,651

(22) PCT Filed: Aug. 11, 2008

(86) PCT No.: PCT/US2008/009635
§ 371 (c)(1),
(2), (4) Date: Mar. 21, 2011

(87) PCT Pub. No.: WO2009/020667
PCT Pub. Date: Feb. 12, 2009

(65) Prior Publication Data
US 2011/0160472 A1 Jun. 30, 2011

Related U.S. Application Data

(60) Provisional application No. 60/964,183, filed on Aug. 9, 2007.

(51) Int. Cl.
C07C 2/00 (2006.01)
C11B 3/02 (2006.01)

(52) U.S. Cl.
USPC ........... 585/500; 554/175; 554/189; 554/190; 554/191; 554/195; 554/196; 554/161; 585/639

(58) Field of Classification Search
None
See application file for complete search history.

(56) References Cited

U.S. PATENT DOCUMENTS

| | | | |
|---|---|---|---|
| 2,190,593 A * | 2/1940 | Clayton | 554/189 |
| 2,411,822 A * | 11/1946 | Doumani | 585/362 |
| 5,091,116 A | 2/1992 | Krishnamurthy et al. | |
| 5,298,271 A | 3/1994 | Takashina et al. | |
| 5,298,638 A * | 3/1994 | Toeneboehn et al. | 554/191 |
| 5,348,755 A | 9/1994 | Roy | |
| 5,374,751 A | 12/1994 | Cheng et al. | |
| 5,391,385 A | 2/1995 | Seybold | |
| 5,401,866 A | 3/1995 | Cheng et al. | |
| 5,432,083 A | 7/1995 | Copeland et al. | |
| 5,484,201 A | 1/1996 | Goolsbee | |
| 5,532,163 A | 7/1996 | Yagi et al. | |
| 5,560,950 A | 10/1996 | Conte et al. | |
| 5,597,600 A | 1/1997 | Munson et al. | |
| 5,653,966 A | 8/1997 | Bertoli et al. | |
| 5,824,354 A | 10/1998 | Ritter et al. | |
| 5,932,261 A | 8/1999 | Unnithan | |
| 5,959,129 A | 9/1999 | Van Dam et al. | |
| 6,033,706 A | 3/2000 | Silkeberg et al. | |
| 6,129,945 A | 10/2000 | Awad et al. | |
| 6,162,480 A | 12/2000 | Van Buuren et al. | |
| 6,166,279 A * | 12/2000 | Schwab et al. | 585/324 |
| 6,172,248 B1 | 1/2001 | Copeland et al. | |
| 6,207,209 B1 | 3/2001 | Jirjis et al. | |
| 6,210,732 B1 | 4/2001 | Papanton | |
| 6,248,911 B1 | 6/2001 | Canessa et al. | |
| 6,251,460 B1 | 6/2001 | Ganguli et al. | |
| 6,368,648 B1 | 4/2002 | Bertram et al. | |
| 6,552,208 B1 | 4/2003 | Alander et al. | |
| 6,638,551 B1 | 10/2003 | Levy et al. | |
| 6,706,299 B2 | 3/2004 | Thengumpillil et al. | |
| 6,740,134 B2 | 5/2004 | Angelico et al. | |
| 6,800,316 B1 | 10/2004 | Perrut et al. | |
| 6,833,149 B2 | 12/2004 | Jirjis et al. | |
| 6,900,347 B2 | 5/2005 | Paulson et al. | |
| 6,998,050 B2 | 2/2006 | Nakajoh et al. | |
| 7,060,316 B2 | 6/2006 | Sakai et al. | |
| 7,141,083 B2 | 11/2006 | Jordan | |
| 7,144,433 B2 | 12/2006 | Jordan | |
| 7,144,435 B2 | 12/2006 | Jordan | |
| 7,160,338 B2 | 1/2007 | Jordan | |
| 7,160,339 B2 | 1/2007 | Jordan | |
| 7,220,289 B2 | 5/2007 | Jordan | |
| 7,320,809 B2 | 1/2008 | Friedman et al. | |
| 7,576,227 B2 | 8/2009 | Lysenko et al. | |
| 7,597,783 B2 | 10/2009 | Kruidenberg | |
| 7,598,407 B2 | 10/2009 | Kruidenberg | |
| 2005/0154221 A1 | 7/2005 | Lysenko et al. | |

FOREIGN PATENT DOCUMENTS

| | | | |
|---|---|---|---|
| EP | 0116408 | * | 8/1984 |
| WO | WO 00/68347 A1 | | 11/2000 |
| WO | WO 03/093215 A1 | | 11/2003 |
| WO | WO 2006/052688 A2 | | 5/2006 |
| WO | WO 2007/081987 A2 | | 7/2007 |
| WO | WO 2009/007234 A1 | | 1/2009 |
| WO | WO 2009/020665 A1 | | 2/2009 |

OTHER PUBLICATIONS

Erhan, S.Z. et al., Drying properties of metathethesized soybean oil, 1997, JAOCS, vol. 74, No. 6, pp. 703-706.*
Buckler, S.A., et al., Phosphine as a reducig agent, 1962, Journal of organic chemistry, vol. 27, No. 3, pp. 794-798.*
Burfield, D., Deperoxidation of ethers. A novel application of self-indicating molecular sieves, 1982, J. Org. Chem., vol. 47, No. 20, pp. 3821-3824.*
International Search Report and Written Opinion of the International Searching Authority for International Application No. PCT/US2008/009635, dated Oct. 27, 2008, 5 pages.
U.S. Appl. No. 12/672,652, filed Feb. 8, 2010, Uptain et al.
Helme, Jean-Paul, "Soybean Oil Refining," American Soybean Association, 1984, 37 pages.
Extended European Search Report for European Application No. 08795241.2, dated Sep. 2, 2013, 7 pages.

* cited by examiner

Primary Examiner — Yate K Cutliff
(74) Attorney, Agent, or Firm — Brinks, Gilson & Lione

(57) ABSTRACT

Various methods are provided for metathesizing a feedstock. In one aspect, a method includes providing a feedstock comprising a natural oil, chemically treating the feedstock under conditions sufficient to diminish catalyst poisons in the feedstock, and, following the treating, combining a metathesis catalyst with the feedstock under conditions sufficient to metathesize the feedstock.

24 Claims, No Drawings

CHEMICAL METHODS FOR TREATING A METATHESIS FEEDSTOCK

RELATED APPLICATIONS

This application is a national application filed under 35 USC §371 of International Application No. PCT/US2008/009635, filed Aug. 11, 2008, which claims the benefit of U.S. Provisional Patent Application Ser. No. 60/964,183, filed Aug. 9, 2007, which are incorporated herein by reference.

TECHNICAL FIELD

This application relates to metathesis reactions and, in particular, to methods of improving catalyst performance in a metathesis reaction of a natural feedstock.

BACKGROUND OF THE INVENTION

Metathesis is a chemical process that is generally known in the art. Metathesis is a catalytic reaction that involves the interchange of alkylidene units among compounds containing one or more double bonds (e.g., olefinic compounds) via the formation and cleavage of the carbon-carbon double bonds. Metathesis may occur between two like molecules (often referred to as self-metathesis) and/or it may occur between two different molecules (often referred to as cross-metathesis). Self-metathesis may be represented schematically as shown in Equation I.

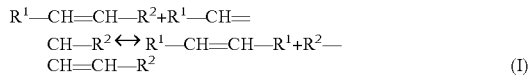

(I)

wherein $R^1$ and $R^2$ are organic groups.

Cross-metathesis may be represented schematically as shown in Equation II.

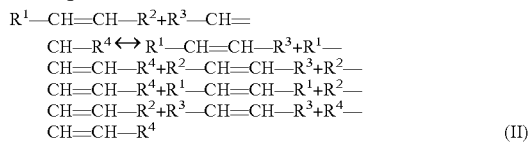

(II)

wherein $R^1$, $R^2$, $R^3$, and $R^4$ are organic groups.

In recent years, there has been an increased demand for environmentally friendly techniques for manufacturing materials typically derived from petroleum sources. For example, researchers have been studying the feasibility of manufacturing waxes, plastics, and the like, using natural feedstocks, such as vegetable and seed-based oils. In one example, metathesis catalysts are used to manufacture candle wax, as described in PCT/US 2006/000822, which is herein incorporated by reference. Metathesis reactions involving natural feedstocks offer promising solutions for today and for the future.

Natural feedstocks of interest typically include, for example, natural oils (e.g., vegetable oils, fish oil, animal fats) and derivatives of natural oils, such as fatty acids and fatty acid alkyl (e.g., methyl) esters. These feedstocks may be converted into industrially useful chemicals (e.g., waxes, plastics, cosmetics, biofuels, etc.) by any number of different metathesis reactions. Significant reaction classes include, for example, self-metathesis, cross-metathesis with olefins, and ring-opening metathesis reactions. Representative examples of useful metathesis catalysts are provided below. Metathesis catalysts can be expensive and, therefore, it is desirable to improve the efficiency of the metathesis catalyst.

Catalyst efficiency and product conversion can vary dramatically depending on the purity of the feedstock that is being metathesized. One of the challenges with using natural feedstocks is that naturally-derived feedstocks may include impurities, sometimes in trace amounts, that do not exist in petroleum feedstocks. These impurities often react with the metathesis catalyst and may drastically affect the efficiency of the catalyst and metathesis reaction. Moreover, the presence and level of various impurities in natural oils may vary from batch-to-batch, depending, for example, on the geographic location of the harvest, and even on the specific field of harvest as well as other growing conditions.

BRIEF SUMMARY OF THE INVENTION

The present invention is a method metathesizing a feedstock. The method comprises providing a feedstock comprising a natural oil. The method further comprises chemically treating the feedstock under conditions sufficient to diminish catalyst poisons in the feedstock. The method further comprises combining a metathesis catalyst with the feedstock under conditions sufficient to metathesize the feedstock.

In another aspect, the method comprises providing a feedstock comprising a natural oil. The method further comprises chemically treating the feedstock under conditions sufficient to diminish non-peroxide poisons in the feedstock. The method further comprises combining a metathesis catalyst with the feedstock under conditions sufficient to metathesize the feedstock.

In another aspect, the method comprises providing a feedstock comprising a natural oil. The feedstock has a starting peroxide value. The method further comprises chemically treating the feedstock for a time sufficient to reduce the starting peroxide value of the feedstock by approximately 80% or more. The method further comprises combining a metathesis catalyst with the feedstock under conditions sufficient to metathesize the feedstock.

DETAILED DESCRIPTION OF THE INVENTION

The present application relates to treatment of metathesis feedstocks. Such treatments, which remove harmful catalyst poisons, are conducted prior to introducing a metathesis catalyst, thereby improving metathesis catalyst performance. Exemplary feedstocks may include natural oils.

As used herein, the singular forms "a," "an," and "the" include plural referents unless the context clearly dictates otherwise. For example, reference to "a substituent" encompasses a single substituent as well as two or more substituents, and the like.

As used herein, the terms "for example," "for instance," "such as," or "including" are meant to introduce examples that further clarify more general subject matter. Unless otherwise specified, these examples are provided only as an aid for understanding the applications illustrated in the present disclosure, and are not meant to be limiting in any fashion.

As used herein, the term "metathesis catalyst" includes any catalyst or catalyst system that catalyzes a metathesis reaction.

As used herein, the term "natural oil" or "natural feedstock" refers to an oil derived from a plant or animal source. The term "natural oil" includes natural oil derivatives, unless otherwise indicated. Examples of natural oils include, but are not limited to, vegetable oils, algae oils, animal fats, tall oils, derivatives of these oils, combinations of any of these oils, and the like. Representative examples of vegetable oils include canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, and castor oil. Representative examples of animal fats include lard, tallow, chicken fat, yellow grease, and fish oil. Tall oils are by-products of wood pulp manufacture.

As used herein, the term "natural oil derivatives" refers to the compounds or mixture of compounds derived from the natural oil using any one or combination of methods known in the chemical arts. Such methods include saponification, esterification, hydrogenation (partial or full), isomerization, oxidation, and reduction. For example, the natural oil derivative may be a fatty acid methyl ester (FAME) derived from the glyceride of the natural oil. Representative examples of natural oil derivatives include fatty acids and fatty acid alkyl (e.g., methyl) esters of the natural oil. In some preferred embodiments, a feedstock may include canola or soybean oil, for example, refined, bleached, and deodorized soybean oil (i.e., RBD soybean oil). Soybean oil is an unsaturated polyol ester of glycerol that typically comprises about 95% weight or greater (e.g., 99% weight or greater) triglycerides of fatty acids. Major fatty acids in the polyol esters of soybean oil include saturated fatty acids, for example, palmitic acid (hexadecanoic acid) and stearic acid (octadecanoic acid), and unsaturated fatty acids, for example, oleic acid (9-octadecenoic acid), linoleic acid (9,12-octadecadienoic acid), and linolenic acid (9,12,15-octadecatrienoic acid).

As used herein, the term "catalyst poison" includes any chemical species or impurity in a feedstock that reduces or is capable of reducing the functionality (e.g., efficiency, conversion, turnover number) of the metathesis catalyst. The term "turnover number" or "catalyst turnover" generally refers to the number of moles of feedstock that a mole of catalyst can convert before becoming deactivated.

As used herein, the term "peroxides" includes any and all peroxides, such as hydrogen peroxides, unless indicated otherwise.

As used herein, the term "non-peroxide poisons," or "other catalyst poisons," refers to catalyst poisons other than peroxides that may be found in natural oil feedstocks. These non-peroxide poisons include, but are not limited to, water, aldehydes, alcohols, byproducts from oxidative degradation, terminal conjugated polyenes, free fatty acids, free glycerin, aliphatic alcohols, nitriles, esters with unsaturated groups near ester groups, d-sphingosine, and additional impurities, including "color bodies." Examples of "color bodies" include trace impurities such as indanes, naphthalenes, phenanthrenes, pyrene, alkylbenzenes, and the like.

As used herein, the term "adsorbent" refers to any material or substance that is used, or that may be used, to absorb or adsorb another material or substance and includes solid, liquid, and gaseous absorbents and adsorbents.

As used herein, the term "catalyst efficiency" is defined as the percent conversion of feedstock and is measured by the GC-analysis of transesterified products, as described below.

As used herein, the term "maximum theoretical limit" or "maximum theoretical conversion limit" refers to the apparent maximum feedstock conversion determined through GC-analysis. For each metathesis reaction, there is a minimum catalyst loading amount required to achieve the maximum theoretical limit. Any increase in catalyst loading beyond this minimum loading will not improve conversion. Additionally, no amount of treatment to remove catalyst poisons will improve conversion beyond the maximum theoretical conversion limit. It is noted that different natural oil feedstocks may have different maximum theoretical conversion limits. Additionally, a particular feedstock may have a different maximum theoretical conversion limits based upon the type of metathesis reaction that the feedstock undergoes (cross- v. self-metathesis). For example, based upon experimental data, self-metathesis of a soybean oil derivative has a maximum theoretical conversion limit of approximately 70%.

As used herein, the terms "metathesize" and "metathesizing" refer to the reacting of a feedstock in the presence of a metathesis catalyst to form a metathesis product comprising a new olefinic compound. Metathesizing may refer to cross-metathesis (a.k.a. co-metathesis), self-metathesis, ring-opening metathesis, ring-opening metathesis polymerizations (ROMP), ring-closing metathesis (RCM), and acyclic diene metathesis (ADMET). For example, metathesizing may refer to reacting two of the same triglycerides present in a natural feedstock (self-metathesis) in the presence of a metathesis catalyst, wherein each triglyceride has an unsaturated carbon-carbon double bond, thereby forming two new olefinic molecules which may include a dimer of the triglyceride. Additionally, metathesizing may refer to reacting an olefin, such as ethylene, and a triglyceride in a natural feedstock having at least one unsaturated carbon-carbon double bond, thereby forming two new olefinic molecules (cross-metathesis).

The presence and level of various impurities for natural oils may vary from location-to-location, field-to-field, or batch-to-batch. It may be difficult to predict the presence or level of certain impurities in the natural oil feedstock without extensive testing on each batch. Accordingly, it is important to be able to design a robust treatment for the various natural oil feedstocks with varying levels of impurities in order to diminish the impurities and improve catalyst performance and product conversion. As seen in the examples below, natural feedstocks have varying levels of peroxide impurities. Typically, the natural oil feedstock may have a peroxide value greater than 1 milliequivalent per 1000 g of feedstock (meq/kg). Typical peroxide values may be greater than 10 meq/kg. Food grade natural oils typically have relatively low peroxide values, closer to 1 meq/kg. Industrial grade natural oils or fatty acid methyl esters of natural oils typically have higher peroxide values. Based upon these examples for the fatty acid methyl esters of soybean and canola oil, the starting peroxide value is typically greater than 5 milliequivalents per 1000 g of feedstock (meq/kg). Examples also show that fatty acid methyl esters of a natural oil may exceed 10 meq/kg.

The inventors have discovered that catalyst efficiency may be greatly improved using chemical techniques to treat a natural feedstock. Metathesis catalyst poisons may be diminished by chemically treating the feedstock prior to introducing the metathesis catalyst to the feedstock. A chemical treatment may target metathesis catalysts poisons, including peroxides. The inventors have discovered that peroxides are strongly correlated with catalyst efficiency and turnover. This may indicate that peroxides are a significant catalyst poison. Additionally, the inventors have discovered that such treatments also appear to target and react with other, non-peroxide, catalyst poisons, rendering them inactive. The inventors have also discovered that treatment of a natural oil feedstock with a low starting peroxide value (e.g., <1 meq/kg) is capable of improving catalyst efficiency and turnover, indicating that while peroxide value is an important measure of feedstock quality, it is not the only factor.

Various methods are disclosed that include exposing a metathesis feedstock material (e.g., a vegetable oil) to a chemical treatment in order to diminish metathesis catalyst poisons. Examples of chemical treatments may include various types of reducing agents, such as sulfite (such as sodium bisulfite), borohydride (such as sodium borohydride), phosphine, thiosulfate, and phosphate. In some preferred examples, sodium bisulfite or sodium borohydride is used as the reducing agent. Reducing agents may react with the peroxides and other catalyst poisons to reduce the poisons into aldehydes, and other water-soluble complexes.

In other embodiments, a chemical treatment may comprise treatment with an inorganic base (such as carbonate, bicarbonate, or hydroxide) coupled with a cation (such as calcium or barium). In such a chemical treatment, the cation-inorganic base reacts with anions (potential catalyst poisons) to create insoluble salts. Potential anions present in a natural feedstock include soaps, phosphates, sulfates, and the like. The insoluble salts precipitate out of solution to be filtered away from the feedstock. Such a process provides a cleaner feedstock for the metathesis reaction. A preferred embodiment of a cation-inorganic base is calcium hydroxide.

In preferred embodiments, the chemical treatment includes combining a chemical, as described above, in an amount that is 5 wt % or less than the feedstock, 3 wt % or less of the feedstock, 2 wt % or less of the feedstock, and more preferably, 1 wt % or less of the feedstock.

In preferred embodiments, the chemical treatment is conducted at a temperature between 0° C. and 100° C., between approximately 25° C. and 90° C., and more preferably, between approximately 50° C. and 80° C.

In preferred embodiments, the chemical treatment diminishes the peroxide level in the feedstock to less than 1 meq/kg, and more preferably, less than 0.5 meq/kg. In some circumstances, for example when the peroxide value of the feedstock is greater than 5 meq/kg, it may be preferable to diminish the level of peroxides by approximately 80% or more or approximately 90% or more. In some circumstances, for example where the feedstock has a starting peroxide value that is greater than 10 meq/kg, it may be preferable to diminish the level of peroxides by approximately 90% or more or approximately 95% or more.

The methods may be used to diminish the amount of metathesis catalyst poisons in metathesis feedstocks. This allows metathesis feedstocks prepared in accordance with the methods to be metathesized at a high turnover number of the metathesis catalyst. In other words, diminishing catalyst poisons may assist in improvement to the catalyst efficiency and conversion.

By chemically treating the feedstock, the reduction in catalyst poisons will improve feedstock conversion, and allow the opportunity to decrease catalyst loading. This is particularly desirable due to the high costs associated with typical metathesis catalysts. In some preferred embodiments, a metathesis reaction may catalyze the metathesis of at least 50% of the maximum theoretical conversion limit with a catalyst loading of 30 ppm or less per mol of carbon-carbon double bonds in the feedstock ("ppm/db"). For example, if the maximum theoretical conversion limit is 70% of the feedstock, it is preferable to catalyze or convert at least 35% of the feedstock (35/70=50%). A 50% or greater conversion of the maximum theoretical limit with 15 ppm/db or less is more preferable. A 50% or greater conversion of the maximum theoretical limit with 10 ppm/db or less is even more preferable. A 50% or more conversion of the maximum theoretical limit with 5 ppm/db or less is even more preferable. A 50% or greater conversion of the maximum theoretical limit with 3 ppm/db or less is even more preferable. A 50% or greater conversion of the maximum theoretical limit with 2 ppm/db or less is even more preferable.

In some preferred embodiments, a metathesis reaction may catalyze the metathesis of at least 70% of the maximum theoretical conversion limit with a catalyst loading of 30 ppm or less per mol of carbon-carbon double bonds in the feedstock ("ppm/db"). A 70% or greater conversion of the maximum theoretical limit with 15 ppm/db or less is more preferable. A 70% or greater conversion of the maximum theoretical limit with 10 ppm/db or less is even more preferable. A 70% or more conversion of the maximum theoretical limit with 5 ppm/db or less is even more preferable. A 70% or greater conversion of the maximum theoretical limit with 3 ppm/db or less is even more preferable. A 70% or greater conversion of the maximum theoretical limit with 2 ppm/db or less is even more preferable.

In some preferred embodiments, a metathesis reaction may catalyze the metathesis of at least 85% of the maximum theoretical conversion limit with a catalyst loading of 30 ppm or less per mol of carbon-carbon double bonds in the feedstock ("ppm/db"). An 85% or greater conversion of the maximum theoretical limit with 15 ppm/db or less is more preferable. An 85% or greater conversion of the maximum theoretical limit with 10 ppm/db or less is even more preferable. An 85% or more conversion of the maximum theoretical limit with 5 ppm/db or less is even more preferable. An 85% or greater conversion of the maximum theoretical limit with 3 ppm/db or less is even more preferable. An 85% or greater conversion of the maximum theoretical limit with 2 ppm/db or less is even more preferable.

In some preferred embodiments, at very low catalyst loadings of 1 ppm/db, a metathesis reaction may catalyze the metathesis of at least 30% conversion of the maximum theoretical limit. A 40% or greater conversion of the maximum theoretical limit with 1 ppm/db or less is even more preferable. A 50% or more conversion of the maximum theoretical limit with 1 ppm/db or less is even more preferable. A 60% or greater conversion of the maximum theoretical limit with 1 ppm/db or less is even more preferable.

In one example, the metathesis feedstock may be treated with sodium bisulfite in order to diminish metathesis catalyst poisons. Sodium bisulfite is a reducing agent that may react with peroxides and reduce the peroxides into aldehydes. Bisulfite will further react with aldehydes to form a water-soluble complex. The inventors discovered a strong correlation between peroxide levels and catalyst activity. Accordingly, chemical treatments that selectively target peroxides are particularly advantageous. Additionally, chemical treatment by sodium bisulfite may potentially remove other non-peroxide poisons as well, further improving catalyst activity. For example, species like aldehydes may also have an impact on catalyst activity, so it may be helpful to diminish them as well.

The bisulfite may be prepared as an aqueous solution. It is then mixed with the feedstock under a nitrogen environment or under vacuum. Heating the solution during mixing may accelerate the reaction. The heating is preferably conducted in an oxygen-free environment to prevent formation of additional peroxides. Additionally, it may be desirable to limit the water content in the natural oil in order to limit the amount of poisons created during or after the chemical reaction.

Preferred reaction temperatures may range from about 25° C. to about 90° C. It is even more preferable that the temperature range from about 50° C. to about 70° C. Sufficient hold time should be provided to allow the reaction to proceed to completion. The necessary hold time will depend, for example, on mixing intensity and on reaction temperature.

The sodium bisulfite is preferably added in an amount less than 5 wt % of the feedstock. It is more preferable that the addition of the sodium bisulfite comprise 3 wt % or less of the feedstock. It is more preferable that the addition of the sodium bisulfite comprise 2 wt % or less of the feedstock. It is even more preferable that the addition of the sodium bisulfite comprise 1 wt % or less of the feedstock. Additionally, it is preferable to add approximately 0.1 wt % or more sodium bisulfite to the feedstock.

In some embodiments, a high-intensity mixer may be used in order to accelerate the rate of reaction. Examples of such devices include high shear mixers, centrifugal reactors, etc.

After the sodium bisulfite treatment, the feedstock may be washed with water to remove the excess bisulfite and byproducts from the reactions. One or more washing steps may be used. During each washing step, a water phase and an organic phase may form. The water phase may be separated from the organic phase by gravity settling, by centrifugation, or by other means of liquid-liquid separation, which are known to those skilled in the art. The organic phase (i.e. the chemically treated feedstock) may then be dried to remove residual traces of water. A vacuum flash dryer or other suitable means may be used to accomplish the removal of trace water.

As seen in the examples below, the natural oil feedstocks typically have a starting peroxide value (PV) that ranges from approximately 1 milliequivalent per 1000 g feedstock (meq/kg) to more than 10 meq/kg. Chemical treatment with sodium bisulfite preferably diminishes the peroxide value in the feedstock to less than 1 meq/kg. It is more preferable to reduce the peroxide value to less than 0.5 meq/kg. In circumstances where the feedstock has a starting peroxide value that is greater than 5 meq/kg, it is preferable to diminish the level of peroxides with a sodium bisulfite treatment by approximately 80% or more. It is more preferable to diminish the level of peroxides with a sodium bisulfite treatment by approximately 90% or more. In circumstances where the feedstock has a starting peroxide value that is greater than 10 meq/kg, it is preferable to diminish the level of peroxides with a sodium bisulfite treatment by approximately 90% or more. It is more preferable to diminish the level of peroxides with a sodium bisulfite treatment by approximately 95% or more.

The chemically treated feedstock is preferably sparged with nitrogen in order to remove any oxygen that was added by water washing. Preferably, the chemically treated feedstock may be stored under nitrogen until it is ready for use in a metathesis reaction, such as self-metathesis, cross-metathesis, or ring-opening metathesis.

When the metathesis reaction is conducted, it is desired that a diminished level of catalyst poisons based upon the sodium bisulfite chemical treatment will result in an improved feedstock conversion at a lower catalyst loading. In some preferred examples, a metathesis reaction may catalyze the metathesis of at least 50% of the maximum theoretical conversion limit with a catalyst loading of 30 ppm or less per mol of carbon-carbon double bonds in the feedstock ("ppm/db"). A 50% or greater conversion of the maximum theoretical limit with 15 ppm/db or less is more preferable. A 50% or greater conversion of the maximum theoretical limit with 10 ppm/db or less is even more preferable. A 50% or more conversion of the maximum theoretical limit with 5 ppm/db or less is even more preferable. A 50% or greater conversion of the maximum theoretical limit with 3 ppm/db or less is even more preferable. A 50% or greater conversion of the maximum theoretical limit with 2 ppm/db or less is even more preferable.

In some preferred embodiments, a metathesis reaction may catalyze the metathesis of at least 70% of the maximum theoretical conversion limit with a catalyst loading of 30 ppm or less per mol of carbon-carbon double bonds in the feedstock ("ppm/db"). A 70% or greater conversion of the maximum theoretical limit with 15 ppm/db or less is more preferable. A 70% or greater conversion of the maximum theoretical limit with 10 ppm/db or less is even more preferable. A 70% or more conversion of the maximum theoretical limit with 5 ppm/db or less is even more preferable. A 70% or greater conversion of the maximum theoretical limit with 3 ppm/db or less is even more preferable. A 70% or greater conversion of the maximum theoretical limit with 2 ppm/db or less is even more preferable.

In some preferred embodiments, a metathesis reaction may catalyze the metathesis of at least 85% of the maximum theoretical conversion limit with a catalyst loading of 30 ppm or less per mol of carbon-carbon double bonds in the feedstock ("ppm/db"). An 85% or greater conversion of the maximum theoretical limit with 15 ppm/db or less is more preferable. An 85% or greater conversion of the maximum theoretical limit with 10 ppm/db or less is even more preferable. An 85% or more conversion of the maximum theoretical limit with 5 ppm/db or less is even more preferable. An 85% or greater conversion of the maximum theoretical limit with 3 ppm/db or less is even more preferable. An 85% or greater conversion of the maximum theoretical limit with 2 ppm/db or less is even more preferable.

In some preferred embodiments, at very low catalyst loadings of 1 ppm/db, a metathesis reaction may catalyze the metathesis of at least 30% conversion of the maximum theoretical limit. A 40% or greater conversion of the maximum theoretical limit with 1 ppm/db or less is even more preferable. A 50% or more conversion of the maximum theoretical limit with 1 ppm/db or less is even more preferable. A 60% or greater conversion of the maximum theoretical limit with 1 ppm/db or less is even more preferable.

In another embodiment, a metathesis feedstock may be treated with sodium borohydride in order to diminish metathesis catalyst poisons. Sodium borohydride is a strong reducing agent that will chemically reduce peroxides into aldehydes. It will further chemically reduce aldehydes into alcohols. The borohydride may also react with other species present in the feedstock, such as color bodies, free fatty acids, and free glycerin. These additional reactions may also be beneficial to improve catalyst activity or feedstock conversion.

The sodium borohydride is preferably added in an amount less than 5 wt % of the feedstock. It is more preferable that the addition of the sodium borohydride comprise 3 wt % or less of the feedstock. It is more preferable that the addition of the sodium borohydride comprise 2 wt % or less of the feedstock. It is even more preferable that the addition of the sodium borohydride comprise 1 wt % or less of the feedstock. Additionally, it is preferable to add approximately 0.1 wt % or more sodium borohydride to the feedstock.

According to the method, sodium borohydride may be added directly to the feedstock and mixed under a nitrogen environment or under vacuum. The temperature may then be increased to accelerate the reaction. Preferred temperatures preferably range from about 25° C. to about 90° C. It is even more preferable that the temperature range from about 50° C. to about 80° C. Hold time is provided to ensure complete reaction. The amount of hold time needed will typically depend on the reaction temperature and mixing intensity. In some embodiments, a high-intensity mixer may be used in order to accelerate the rate of reaction. Examples of such devices include high shear mixers, centrifugal reactors, etc.

After sodium borohydride treatment, the feedstock may be washed with water to remove the excess borohydride and byproducts from the reactions.

As seen in the examples below, the natural oil feedstocks typically have a starting peroxide value (PV) that ranges from approximately 1 milliequivalent per 1000 g feedstock (meq/kg) to more than 10 meq/kg. Chemical treatment with sodium borohydride, it is preferable to diminish the peroxide value in the feedstock to less than 1 meq/kg. It is more preferable to reduce the peroxide value to less than 0.5 meq/kg. In circumstances where the feedstock has a starting peroxide value that is greater than 5 meq/kg, it is preferable to diminish the level of peroxides with a sodium borohydride treatment by approximately 80% or more. It is more preferable to diminish the level of peroxides with a sodium borohydride treatment by approximately 90% or more. In circumstances where the feedstock has a starting peroxide value that is greater than 10 meq/kg, it is preferable to diminish the level of peroxides with a sodium borohydride treatment by approximately 90% or more. It is more preferable to diminish the level of peroxides with a sodium borohydride treatment by approximately 95% or more.

The chemically treated feedstock may be sparged with nitrogen in order to remove any oxygen that was added by water washing. Preferably, the chemically treated feedstock may be stored under nitrogen until it is ready for use in a metathesis reaction, such as self-metathesis, cross-metathesis, or ring-opening metathesis.

When the metathesis reaction is conducted, it is desired that a diminished level of catalyst poisons based upon the sodium borohydride chemical treatment will result in an improved feedstock conversion at a lower catalyst loading. In some preferred embodiments, a metathesis reaction may catalyze the metathesis of at least 50% of the maximum theoretical conversion limit with a catalyst loading of 30 ppm or less per mol of carbon-carbon double bonds in the feedstock ("ppm/db"). A 50% or greater conversion of the maximum theoretical limit with 15 ppm/db or less is more preferable. A 50% or greater conversion of the maximum theoretical limit with 10 ppm/db or less is even more preferable. A 50% or more conversion of the maximum theoretical limit with 5 ppm/db or less is even more preferable. A 50% or greater conversion of the maximum theoretical limit with 3 ppm/db or less is even more preferable. A 50% or greater conversion of the maximum theoretical limit with 2 ppm/db or less is even more preferable.

In some preferred embodiments, a metathesis reaction may catalyze the metathesis of at least 70% of the maximum theoretical conversion limit with a catalyst loading of 30 ppm or less per mol of carbon-carbon double bonds in the feedstock ("ppm/db"). A 70% or greater conversion of the maximum theoretical limit with 15 ppm/db or less is more preferable. A 70% or greater conversion of the maximum theoretical limit with 10 ppm/db or less is even more preferable. A 70% or more conversion of the maximum theoretical limit with 5 ppm/db or less is even more preferable. A 70% or greater conversion of the maximum theoretical limit with 3 ppm/db or less is even more preferable. A 70% or greater conversion of the maximum theoretical limit with 2 ppm/db or less is even more preferable.

In some preferred embodiments, a metathesis reaction may catalyze the metathesis of at least 85% of the maximum theoretical conversion limit with a catalyst loading of 30 ppm or less per mol of carbon-carbon double bonds in the feedstock ("ppm/db"). An 85% or greater conversion of the maximum theoretical limit with 15 ppm/db or less is more preferable. An 85% or greater conversion of the maximum theoretical limit with 10 ppm/db or less is even more preferable. An 85% or more conversion of the maximum theoretical limit with 5 ppm/db or less is even more preferable. An 85% or greater conversion of the maximum theoretical limit with 3 ppm/db or less is even more preferable. An 85% or greater conversion of the maximum theoretical limit with 2 ppm/db or less is even more preferable.

In some preferred embodiments, at very low catalyst loadings of 1 ppm/db, a metathesis reaction may catalyze the metathesis of at least 30% conversion of the maximum theoretical limit. A 40% or greater conversion of the maximum theoretical limit with 1 ppm/db or less is even more preferable. A 50% or more conversion of the maximum theoretical limit with 1 ppm/db or less is even more preferable. A 60% or greater conversion of the maximum theoretical limit with 1 ppm/db or less is even more preferable.

In some embodiments, in addition to a chemical treatment, it may also be desirable to use physical means to diminish the level of poisons in the feedstock. An adsorbent may be added to the feedstock to assist in diminishing the level of catalyst poisons. The adsorbent may be added before, during, or after any of the chemical treatment conditions previously described. Preferably, the adsorbent is added during or after the chemical treatment. More preferably, the adsorbent is added after the chemical treatment. Even more preferably, the adsorbent is added after the temperature of the chemical treatment has been cooled down below approximately 60° C. Even more preferably, the adsorbent is added after the temperature of the chemical treatment has been cooled down below approximately 40° C.

The adsorbent treatment may function in at least two capacities. The adsorbent may assist the chemical treatment process by further reducing catalyst poisons that would not have been successfully removed by chemical treatment alone. Additionally, the adsorbent may be used to remove any residual chemical additives. The adsorbent may also assist in removing various byproducts from the chemical reactions. Preferably, the amount of adsorbent added to the feedstock ranges from about 0.1 wt % to about 5 wt % when used in conjunction with the chemical treatment. More preferably, the amount of adsorbent added to the feedstock ranges from about 0.1 wt % to about 3 wt %. Even more preferably, the amount of adsorbent added to the feedstock ranges from about 0.2 wt % to about 2 wt %.

Additional hold time and mixing is provided for the adsorbent. The necessary hold time will depend on the temperature and mixing intensity. High-intensity mixing may be employed. Typically, the adsorption treatment step is a matter of hours. More preferably, the adsorption treatment is less than an hour. Even more preferably, the time sufficient for the adsorption treatment is a matter of minutes.

Examples of adsorbents which may be used in combination with a chemical treatment include, but are not limited to, molecular sieves, activated carbon, zeolites, silica gel, Fuller's earth, neutral alumina, basic Alumina, Celite, acid-activated clay, aluminum sulfate, calcium carbonate, Kaolin, magnesium sulfate, potassium chloride, potassium magnesium sulfate, potassium sulfate, soda ash, sodium carbonate, sodium sulfate, magnesium silicate, and the like.

In preferred embodiments, the adsorbent is a silicate such as magnesium silicate (e.g., MAGNESOL from The Dallas Group of America, Inc.) may be used as the adsorbent for adsorbing catalyst poisons, chemical additives, and by products, especially any boron-containing compounds. Preferably, the level of magnesium silicate adsorbent ranges from about 0.1 wt % to about 5 wt % when used in conjunction with the chemical treatment. More preferably, the amount of magnesium silicate ranges from about 0.1 wt % to about 3 wt %. Even more preferably, the level of magnesium silicate ranges from about 0.2 wt % to about 2 wt %. Additional hold time and mixing may be provided for the magnesium silicate. Again, the necessary hold time will depend on the temperature and mixing intensity. High intensity mixing may be employed. Typically, the sufficient time for the adsorption treatment step with magnesium silicate is a matter of hours. More preferably, the adsorption treatment with magnesium silicate is less than an hour. Even more preferably, the time sufficient for the adsorption treatment with magnesium silicate is a matter of minutes. The magnesium silicate may be added before, during, or after any of the chemical treatment conditions previously described. Preferably, the magnesium silicate is added during or after the chemical treatment. More preferably, the magnesium silicate is added after the chemical treatment.

The adsorbent may be removed by filtration, centrifugation, pouring or any other method of solid-liquid separation known to those skilled in the art. Optionally, a filter aid, such as Celite, can also be added at the time of adsorbent addition to aid subsequent filtration. The treated feedstock is typically cooled to less than about 40° C. before allowing exposure to air. In some examples of chemical treatment plus adsorbent treatment, the treated feedstock preferably has a diminished peroxide value of less than 1 meq/kg. It is more preferable that the feedstock has a diminished peroxide value of less than 0.5 meq/kg. In circumstances where the feedstock has a starting peroxide value that is greater than 5 meq/kg, it is preferable to diminish the level of peroxides with a chemical and adsorbent treatment by approximately 80% or more. It is more preferable to diminish the level of peroxides with a chemical and adsorbent treatment by approximately 90% or more. In circumstances where the feedstock has a starting peroxide value that is greater than 10 meq/kg, it is preferable to diminish the level of peroxides with a chemical and adsorbent treatment by approximately 90% or more. It is more preferable to diminish the level of peroxides with a chemical and adsorbent treatment by approximately 95% or more.

It should be noted that combining chemical treatment and adsorbent treatment may be more effective in diminishing catalyst poisons than adsorbent treatment alone. Moreover, the combined treatment may also allow for a lower amount of adsorbent to be used in the treatment. When an adsorbent is used by itself, higher quantities of the adsorbent may be needed to achieve similar results in terms of diminished peroxide values. The use of higher quantities of adsorbent adds an undesired cost to the process. Additionally, adsorbent treatment alone may fail to diminish the other non-peroxide catalyst poisons.

After chemical or chemical plus adsorbent treatment, the treated feedstock is then preferably stored under nitrogen until ready for use in a metathesis reaction, such as self-metathesis, cross-metathesis, or ring-opening metathesis.

After the chemical or chemical plus adsorbent treatment, the feedstock may be subjected to a metathesis reaction in the presence of a metathesis catalyst.

The term "metathesis catalyst" includes any catalyst or catalyst system that catalyzes a metathesis reaction. Any known or future-developed metathesis catalyst may be used, alone or in combination with one or more additional catalysts. Exemplary metathesis catalysts include metal carbene catalysts based upon transition metals, for example, ruthenium, molybdenum, osmium, chromium, rhenium, and tungsten. The olefin metathesis catalyst for carrying out the cross-metathesis reactions of the disclosure is preferably a Group 8 transition metal complex having the structure of formula (III)

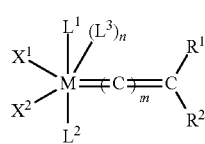

(III)

in which the various substituents are as follows:
M is a Group 8 transition metal;
$L^1$, $L^2$ and $L^3$ are neutral electron donor ligands;
n is 0 or 1, such that $L^3$ may or may not be present;
m is 0, 1, or 2;
$X^1$ and $X^2$ are anionic ligands; and
$R^1$ and $R^2$ are independently selected from hydrogen, hydrocarbyl, substituted hydrocarbyl, heteroatom-containing hydrocarbyl, substituted heteroatom-containing hydrocarbyl, and functional groups,
wherein any two or more of $X^1$, $X^2$, $L^1$, $L^2$, $L^3$, $R^1$, and $R^2$ can be taken together to form a cyclic group, and further wherein any one or more of $X^1$, $X^2$, $L^2$, $L^3$, $R^1$, and $R^2$ may be attached to a support.

Preferred catalysts contain Ru or Os as the Group 8 transition metal, with Ru particularly preferred.

Numerous embodiments of the catalysts useful in the reactions of the disclosure are described in more detail infra. For the sake of convenience, the catalysts are described in groups, but it should be emphasized that these groups are not meant to be limiting in any way. That is, any of the catalysts useful in the disclosure may fit the description of more than one of the groups described herein.

A first group of catalysts, then, are commonly referred to as 1$^{st}$ Generation Grubbs-type catalysts, and have the structure of formula (III). For the first group of catalysts, M and m are as described above, and n, $X^1$, $X^2$, $L^1$, $L^2$, $L^3$, $R^1$, and $R^2$ are described as follows.

For the first group of catalysts, n is 0, and $L^1$ and $L^2$ are independently selected from phosphine, sulfonated phosphine, phosphite, phosphinite, phosphonite, arsine, stibine, ether, amine, amide, imine, sulfoxide, carboxyl, nitrosyl, pyridine, substituted pyridine, imidazole, substituted imidazole, pyrazine, and thioether. Exemplary ligands are trisubstituted phosphines.

$X^1$ and $X^2$ are anionic ligands, and may be the same or different, or are linked together to form a cyclic group, typically although not necessarily a five- to eight-membered ring. In preferred embodiments, $X^1$ and $X^2$ are each independently hydrogen, halide, or one of the following groups: $C_1$-$C_{20}$ alkyl, $C_5$-$C_{24}$ aryl, $C_1$-$C_{20}$ alkoxy, $C_5$-$C_{24}$ aryloxy, $C_2$-$C_{20}$ alkoxycarbonyl, $C_6$-$C_{24}$ aryloxycarbonyl, $C_2$-$C_{24}$ acyl, $C_2$-$C_{24}$ acyloxy, $C_1$-$C_{20}$ alkylsulfonato, $C_5$-$C_{24}$ arylsulfonato, $C_1$-$C_{20}$ alkylsulfanyl, $C_5$-$C_{24}$ arylsulfanyl, $C_1$-$C_{20}$ alkylsulfinyl, or $C_5$-$C_{24}$ arylsulfinyl. Optionally, $X^1$ and $X^2$ may be substituted with one or more moieties selected from $C_1$-$C_{12}$ alkyl, $C_1$-$C_{12}$ alkoxy, $C_5$-$C_{24}$ aryl, and halide, which may, in turn, with the exception of halide, be further substituted with one or more groups selected from halide, $C_1$-$C_6$ alkyl, $C_1$-$C_6$ alkoxy, and phenyl. In more preferred embodiments, $X^1$ and $X^2$ are halide, benzoate, $C_2$-$C_6$ acyl, $C_2$-$C_6$ alkoxycarbonyl, $C_1$-$C_6$ alkyl, phenoxy, $C_1$-$C_6$ alkoxy, $C_1$-$C_6$ alkylsulfanyl, aryl, or $C_1$-$C_6$ alkylsulfonyl. In even more preferred embodiments, $X^1$ and $X^2$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethane-sulfonate. In the most preferred embodiments, $X^1$ and $X^2$ are each chloride.

$R^1$ and $R^2$ are independently selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and functional groups. $R^1$ and $R^2$ may also be linked to form a cyclic group, which may be aliphatic or aromatic, and may contain substituents and/or heteroatoms. Generally, such a cyclic group will contain 4 to 12, preferably 5, 6, 7, or 8 ring atoms.

In preferred catalysts, $R^1$ is hydrogen and $R^2$ is selected from $C_1$-$C_{20}$ alkyl, $C_2$-$C_{20}$ alkenyl, and $C_5$-$C_{24}$ aryl, more preferably $C_1$-$C_6$ alkyl, $C_2$-$C_6$ alkenyl, and $C_5$-$C_{14}$ aryl. Still more preferably, $R^2$ is phenyl, vinyl, methyl, isopropyl, or t-butyl, optionally substituted with one or more moieties selected from $C_1$-$C_6$ alkyl, $C_1$-$C_6$ alkoxy, phenyl, and a functional group Fn as defined earlier herein. Most preferably, $R^2$ is phenyl or vinyl substituted with one or more moieties selected from methyl, ethyl, chloro, bromo, iodo, fluoro, nitro, dimethylamino, methyl, methoxy, and phenyl. Optimally, $R^2$ is phenyl or —C=C(CH$_3$)$_2$.

Any two or more (typically two, three, or four) of $X^1$, $X^2$, $L^1$, $L^2$, $L^3$, $R^1$, and $R^2$ can be taken together to form a cyclic group, as disclosed, for example, in U.S. Pat. No. 5,312,940 to Grubbs et al. When any of $X^1$, $X^2$, $L^1$, $L^2$, $L^3$, $R^1$, and $R^2$ are linked to form cyclic groups, those cyclic groups may contain 4 to 12, preferably 4, 5, 6, 7 or 8 atoms, or may comprise two or three of such rings, which may be either fused or linked. The cyclic groups may be aliphatic or aromatic, and may be heteroatom-containing and/or substituted. The cyclic group may, in some cases, form a bidentate ligand or a tridentate ligand. Examples of bidentate ligands include, but are not limited to, bisphosphines, dialkoxides, alkyldiketonates, and aryldiketonates.

A second group of catalysts, commonly referred to as 2$^{nd}$ Generation Grubbs-type catalysts, have the structure of formula (III), wherein $L^1$ is a carbene ligand having the structure of formula (IV)

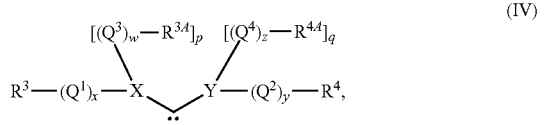

(IV)

such that the complex may have the structure of formula (V)

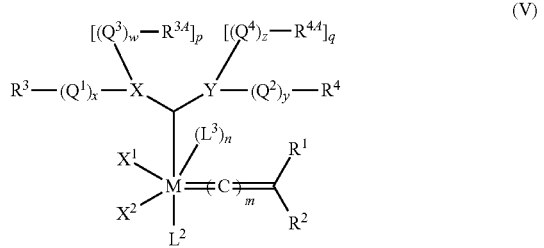

(V)

wherein M, m, n, $X^1$, $X^2$, $L^2$, $L^3$, $R^1$, and $R^2$ are as defined for the first group of catalysts, and the remaining substituents are as follows.

X and Y are heteroatoms typically selected from N, O, S, and P. Since O and S are divalent, p is necessarily zero when X is O or S, and q is necessarily zero when Y is O or S. However, when X is N or P, then p is 1, and when Y is N or P, then q is 1. In a preferred embodiment, both X and Y are N.

$Q^1$, $Q^2$, $Q^3$, and $Q^4$ are linkers, e.g., hydrocarbylene (including substituted hydrocarbylene, heteroatom-containing hydrocarbylene, and substituted heteroatom-containing hydrocarbylene, such as substituted and/or heteroatom-containing alkylene) or —(CO)—, and w, x, y, and z are independently zero or 1, meaning that each linker is optional. Preferably, w, x, y, and z are all zero. Further, two or more substituents on adjacent atoms within $Q^1$, $Q^2$, $Q^3$, and $Q^4$ may be linked to form an additional cyclic group.

$R^3$, $R^{3A}$, $R^4$, and $R^{4A}$ are independently selected from hydrogen, hydrocarbyl, substituted hydrocarbyl, heteroatom-containing hydrocarbyl, and substituted heteroatom-containing hydrocarbyl.

In addition, any two or more of $X^1$, $X^2$, $L^1$, $L^2$, $L^3$, $R^1$, $R^2$, $R^3$, $R^{3A}$, $R^4$, and $R^{4A}$ can be taken together to form a cyclic group, and any one or more of $X^1$, $X^2$, $L^1$, $L^2$, $L^3$, $R^1$, $R^2$, $R^3$, $R^{3A}$, $R^4$, and $R^{4A}$ may be attached to a support.

Preferably, $R^{3A}$ and $R^{4A}$ are linked to form a cyclic group so that the carbene ligand is an heterocyclic carbene and preferably an N-heterocyclic carbene, such as the N-heterocyclic carbene having the structure of formula (VI)

(VI)

where $R^3$ and $R^4$ are defined above, with preferably at least one of $R^3$ and $R^4$, and more preferably both $R^3$ and $R^4$, being alicyclic or aromatic of one to about five rings, and optionally containing one or more heteroatoms and/or substituents. Q is a linker, typically a hydrocarbylene linker, including substituted hydrocarbylene, heteroatom-containing hydrocarbylene, and substituted heteroatom-containing hydrocarbylene linkers, wherein two or more substituents on adjacent atoms within Q may also be linked to form an additional cyclic structure, which may be similarly substituted to provide a fused polycyclic structure of two to about five cyclic groups. Q is often, although again not necessarily, a two-atom linkage or a three-atom linkage.

Examples of N-heterocyclic carbene ligands suitable as $L^1$ thus include, but are not limited to, the following:

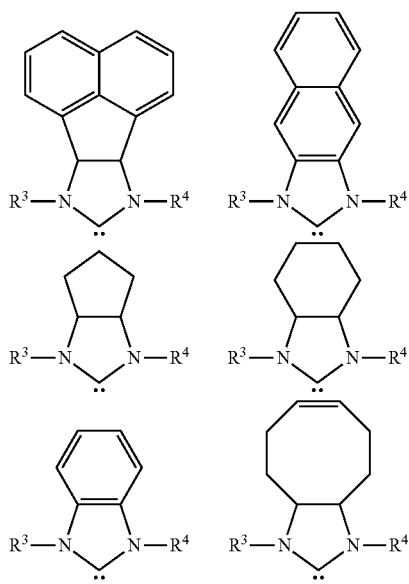

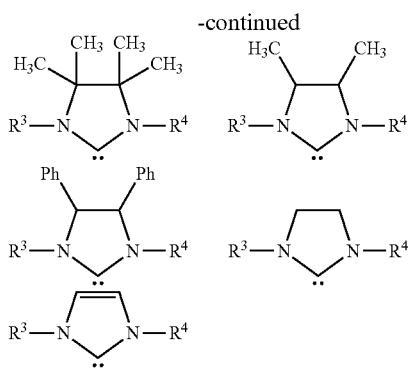

When M is ruthenium, then, the preferred complexes have the structure of formula (VII).

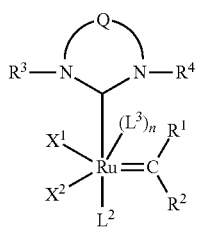

(VII)

In a more preferred embodiment, Q is a two-atom linkage having the structure $-CR^{11}R^{12}-CR^{13}R^{14}-$ or $-CR^{11}=CR^{13}-$, preferably $-CR^{11}R^{12}-CR^{13}R^{14}-$, wherein $R^{11}$, $R^{12}$, $R^{13}$, and $R^{14}$ K are independently selected from hydrogen, hydrocarbyl, substituted hydrocarbyl, heteroatom-containing hydrocarbyl, substituted heteroatom-containing hydrocarbyl, and functional groups. Examples of functional groups here include carboxyl, $C_1$-$C_{20}$ alkoxy, $C_5$-$C_{24}$ aryloxy, $C_2$-$C_{20}$ alkoxycarbonyl, $C_5$-$C_{24}$ alkoxycarbonyl, $C_2$-$C_{24}$ acyloxy, $C_1$-$C_{20}$ alkylthio, $C_5$-$C_{24}$ arylthio, $C_1$-$C_{20}$ alkylsulfonyl, and $C_1$-$C_{20}$ alkylsulfinyl, optionally substituted with one or more moieties selected from $C_1$-$C_{12}$ alkyl, $C_1$-$C_{12}$ alkoxy, $C_5$-$C_{14}$ aryl, hydroxyl, sulfhydryl, formyl, and halide. $R^{11}$, $R^{12}$, $R^{13}$, and $R^{14}$ are preferably independently selected from hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, and substituted phenyl. Alternatively, any two of $R^{11}$, $R^{12}$, $R^{13}$, and $R^{14}$ may be linked together to form a substituted or unsubstituted, saturated or unsaturated ring structure, e.g., a $C_4$-$C_{12}$ alicyclic group or a $C_5$ or $C_6$ aryl group, which may itself be substituted, e.g., with linked or fused alicyclic or aromatic groups, or with other substituents.

When $R^3$ and $R^4$ are aromatic, they are typically although not necessarily composed of one or two aromatic rings, which may or may not be substituted, e.g., $R^3$ and $R^4$ may be phenyl, substituted phenyl, biphenyl, substituted biphenyl, or the like. In one preferred embodiment, $R^3$ and $R^4$ are the same and are each unsubstituted phenyl or phenyl substituted with up to three substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide. Preferably, any substituents present are hydrogen, $C_1$-$C_{12}$ alkyl, $C_1$-$C_{12}$ alkoxy, $C_5$-$C_{14}$ aryl, substituted $C_5$-$C_{14}$ aryl, or halide. As an example, $R^3$ and $R^4$ are mesityl.

In a third group of catalysts having the structure of formula (III), M, m, n, $X^1$, $X^2$, $R^1$, and $R^2$ are as defined for the first group of catalysts, $L^1$ is a strongly coordinating neutral electron donor ligand such as any of those described for the first and second groups of catalysts, and $L^2$ and $L^3$ are weakly coordinating neutral electron donor ligands in the form of optionally substituted heterocyclic groups. Again, n is zero or 1, such that $L^3$ may or may not be present. Generally, in the third group of catalysts, $L^2$ and $L^3$ are optionally substituted five- or six-membered monocyclic groups containing 1 to 4, preferably 1 to 3, most preferably 1 to 2 heteroatoms, or are optionally substituted bicyclic or polycyclic structures composed of 2 to 5 such five- or six-membered monocyclic groups. If the heterocyclic group is substituted, it should not be substituted on a coordinating heteroatom, and any one cyclic moiety within a heterocyclic group will generally not be substituted with more than 3 substituents.

For the third group of catalysts, examples of $L^2$ and $L^3$ include, without limitation, heterocycles containing nitrogen, sulfur, oxygen, or a mixture thereof.

Examples of nitrogen-containing heterocycles appropriate for $L^2$ and $L^3$ include pyridine, bipyridine, pyridazine, pyrimidine, bipyridamine, pyrazine, 1,3,5-triazine, 1,2,4-triazine, 1,2,3-triazine, pyrrole, 2H-pyrrole, 3H-pyrrole, pyrazole, 2H-imidazole, 1,2,3-triazole, 1,2,4-triazole, indole, 3H-indole, 1H-isoindole, cyclopenta(b)pyridine, indazole, quinoline, bisquinoline, isoquinoline, bisisoquinoline, cinnoline, quinazoline, naphthyridine, piperidine, piperazine, pyrrolidine, pyrazolidine, quinuclidine, imidazolidine, picolylimine, purine, benzimidazole, bisimidazole, phenazine, acridine, and carbazole.

Examples of sulfur-containing heterocycles appropriate for $L^2$ and $L^3$ include thiophene, 1,2-dithiole, 1,3-dithiole, thiepin, benzo(b)thiophene, benzo(c)thiophene, thionaphthene, dibenzothiophene, 2H-thiopyran, 4H-thiopyran, and thioanthrene.

Examples of oxygen-containing heterocycles appropriate for $L^2$ and $L^3$ include 2H-pyran, 4H-pyran, 2-pyrone, 4-pyrone, 1,2-dioxin, 1,3-dioxin, oxepin, furan, 2H-1-benzopyran, coumarin, coumarone, chromene, chroman-4-one, isochromen-1-one, isochromen-3-one, xanthene, tetrahydrofuran, 1,4-dioxan, and dibenzofuran.

Examples of mixed heterocycles appropriate for $L^2$ and $L^3$ include isoxazole, oxazole, thiazole, isothiazole, 1,2,3-oxadiazole, 1,2,4-oxadiazole, 1,3,4-oxadiazole, 1,2,3,4-oxatriazole, 1,2,3,5-oxatriazole, 3H-1,2,3-dioxazole, 3H-1,2-oxathiole, 1,3-oxathiole, 4H-1,2-oxazine, 2H-1,3-oxazine, 1,4-oxazine, 1,2,5-oxathiazine, o-isooxazine, phenoxazine, phenothiazine, pyrano[3,4-b]pyrrole, indoxazine, benzoxazole, anthranil, and morpholine.

Preferred $L^2$ and $L^3$ ligands are aromatic nitrogen-containing and oxygen-containing heterocycles, and particularly preferred $L^2$ and $L^3$ ligands are monocyclic N-heteroaryl ligands that are optionally substituted with 1 to 3, preferably 1 or 2, substituents. Specific examples of particularly preferred $L^2$ and $L^3$ ligands are pyridine and substituted pyridines, such as 3-bromopyridine, 4-bromopyridine, 3,5-dibromopyridine, 2,4,6-tribromopyridine, 2,6-dibromopyridine, 3-chloropyridine, 4-chloropyridine, 3,5-dichloropyridine, 2,4,6-trichloropyridine, 2,6-dichloropyridine, 4-iodopyridine, 3,5-diiodopyridine, 3,5-dibromo-4-methylpyridine, 3,5-dichloro-4-methylpyridine, 3,5-dimethyl-4-bromopyridine, 3,5-dimethylpyridine, 4-methylpyridine, 3,5-diisopropylpyridine, 2,4,6-trimethylpyridine, 2,4,6-triisopropylpyridine, 4-(tert-butyl)pyridine, 4-phenylpyridine, 3,5-diphenylpyridine, 3,5-dichloro-4-phenylpyridine, and the like.

In general, any substituents present on $L^2$ and/or $L^3$ are selected from halo, $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, substituted $C_5$-$C_{24}$ heteroaryl, $C_6$-$C_{24}$ alkaryl, substituted $C_6$-$C_{24}$ alkaryl, $C_6$-$C_{24}$ heteroalkaryl, substituted $C_6$-$C_{24}$ heteroalkaryl, $C_6$-$C_{24}$ aralkyl, substituted $C_6$-$C_{24}$ aralkyl, $C_6$-$C_{24}$ heteroaralkyl, substituted $C_6$-$C_{24}$ heteroaralkyl, and functional groups, with suitable functional groups including, without limitation, $C_1$-$C_{20}$ alkoxy, $C_5$-$C_{24}$ aryloxy, $C_2$-$C_{20}$ alkylcarbonyl, $C_6$-$C_{24}$ arylcarbonyl, $C_2$-$C_{20}$ alkylcarbonyloxy, $C_6$-$C_{24}$ arylcarbonyloxy, $C_2$-$C_{20}$ alkoxycarbonyl, $C_6$-$C_{24}$ aryloxycarbonyl, halocarbonyl, $C_2$-$C_{20}$ alkylcarbonato, $C_6$-$C_{24}$ arylcarbonato, carboxy, carboxylato, carbamoyl, mono-($C_1$-$C_{20}$ alkyl)-substituted carbamoyl, di-($C_1$-$C_{20}$ alkyl)-substituted carbamoyl, di-N—($C_1$-$C_{20}$ alkyl), N—($C_5$-$C_{24}$ aryl)-substituted carbamoyl, mono-($C_5$-$C_{24}$ aryl)-substituted carbamoyl, di-($C_6$-$C_{24}$ aryl)-substituted carbamoyl, thiocarbamoyl, mono-($C_1$-$C_{20}$ alkyl)-substituted thiocarbamoyl, di-($C_1$-$C_{20}$ alkyl)-substituted thiocarbamoyl, di-N—($C_1$-$C_{20}$ alkyl)-N—($C_6$-$C_{24}$ aryl)-substituted thiocarbamoyl, mono-($C_6$-$C_{24}$ aryl)-substituted thiocarbamoyl, di-($C_6$-$C_{24}$ aryl)-substituted thiocarbamoyl, carbamido, formyl, thioformyl, amino, mono-($C_1$-$C_{20}$ alkyl)-substituted amino, di-($C_1$-$C_{20}$ alkyl)-substituted amino, mono-($C_5$-$C_{24}$ aryl)-substituted amino, di-($C_5$-$C_{24}$ aryl)-substituted amino, di-N—($C_1$-$C_{20}$ alkyl), N—($C_5$-$C_{24}$ aryl)-substituted amino, $C_2$-$C_{20}$ alkylamido, $C_6$-$C_{24}$ arylamido, imino, $C_1$-$C_{20}$ alkylimino, $C_5$-$C_{24}$ arylimino, nitro, and nitroso. In addition, two adjacent substituents may be taken together to form a ring, generally a five- or six-membered alicyclic or aryl ring, optionally containing 1 to 3 heteroatoms and 1 to 3 substituents as above.

Preferred substituents on $L^2$ and $L^3$ include, without limitation, halo, $C_1$-$C_{12}$ alkyl, substituted $C_1$-$C_{12}$ alkyl, $C_1$-$C_{12}$ heteroalkyl, substituted $C_1$-$C_{12}$ heteroalkyl, $C_5$-$C_{14}$ aryl, substituted $C_5$-$C_{14}$ aryl, $C_5$-$C_{14}$ heteroaryl, substituted $C_5$-$C_{14}$ heteroaryl, $C_6$-$C_{16}$ alkaryl, substituted $C_6$-$C_{16}$ alkaryl, $C_6$-$C_{16}$ heteroalkaryl, substituted $C_6$-$C_{16}$ heteroalkaryl, $C_6$-$C_{16}$ aralkyl, substituted $C_6$-$C_{16}$ aralkyl, $C_6$-$C_{16}$ heteroaralkyl, substituted $C_6$-$C_{16}$ heteroaralkyl, alkoxy, $C_5$-$C_{14}$ aryloxy, $C_2$-$C_{12}$ alkylcarbonyl, $C_6$-$C_{14}$ arylcarbonyl, $C_2$-$C_{12}$ alkylcarbonyloxy, $C_6$-$C_{14}$ arylcarbonyloxy, $C_2$-$C_{12}$ alkoxycarbonyl, $C_6$-$C_{14}$ aryloxycarbonyl, halocarbonyl, formyl, amino, mono-($C_1$-$C_{12}$ alkyl)-substituted amino, di-($C_1$-$C_{12}$ alkyl)-substituted amino, mono-($C_5$-$C_{14}$ aryl)-substituted amino, di-($C_5$-$C_{14}$ aryl)-substituted amino, and nitro.

Of the foregoing, the most preferred substituents are halo, $C_1$-$C_6$ alkyl, $C_1$-$C_6$ haloalkyl, $C_1$-$C_6$ alkoxy, phenyl, substituted phenyl, formyl, N,N-di$C_1$-$C_6$ alkyl)amino, nitro, and nitrogen heterocycles as described above (including, for example, pyrrolidine, piperidine, piperazine, pyrazine, pyrimidine, pyridine, pyridazine, etc.).

$L^2$ and $L^3$ may also be taken together to form a bidentate or multidentate ligand containing two or more, generally two, coordinating heteroatoms such as N, O, S, or P, with preferred such ligands being diimine ligands of the Brookhart type. One representative bidentate ligand has the structure of formula (VIII)

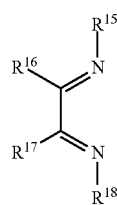

(VIII)

wherein $R^{15}$, $R^{16}$, $R^{17}$ and $R^{18}$ hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), heteroatom-containing hydrocarbyl (e.g., $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or substituted heteroatom-containing hydrocarbyl (e.g., substituted $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or (1) $R^{15}$ and $R^{16}$, (2) $R^{17}$ and $R^{18}$, (3) $R^{16}$ and $R^{17}$, or (4) both $R^{15}$ and $R^{16}$, and $R^{17}$ and $R^{18}$, may be taken together to form a ring, i.e., an N-heterocycle. Preferred cyclic groups in such a case are five- and six-membered rings, typically aromatic rings.

In a fourth group of catalysts that have the structure of formula (III), two of the substituents are taken together to form a bidentate ligand or a tridentate ligand. Examples of bidentate ligands include, but are not limited to, bisphosphines, dialkoxides, alkyldiketonates, and aryldiketonates. Specific examples include —P(Ph)$_2$CH$_2$CH$_2$P(Ph)$_2$-, —As(Ph)$_2$CH$_2$CH$_2$As(Ph$_2$)—, —P(Ph)$_2$CH$_2$CH$_2$C(CF$_3$)$_2$O—, binaphtholate dianions, pinacolate dianions, —P(CH$_3$)$_2$(CH$_2$)$_2$P(CH$_3$)$_2$—, and —OC(CH$_3$)$_2$(CH$_3$)$_2$CO—. Preferred bidentate ligands are —P(Ph)$_2$CH$_2$CH$_2$P(Ph)$_2$- and —P(CH$_3$)$_2$(CH$_2$)$_2$P(CH$_3$)$_2$—. Tridentate ligands include, but are not limited to, (CH$_3$)$_2$NCH$_2$CH$_2$P(Ph)CH$_2$CH$_2$N(CH$_3$)$_2$. Other preferred tridentate ligands are those in which any three of $X^1$, $X^2$, $L^1$, $L^2$, $L^3$, $R^1$, and $R^2$ (e.g., $X^1$, $L^1$, and $L^2$) are taken together to be cyclopentadienyl, indenyl, or fluorenyl, each optionally substituted with $C_2$-$C_{20}$ alkenyl, $C_2$-$C_{20}$ alkynyl, $C_1$-$C_{20}$ alkyl, $C_5$-$C_{20}$ aryl, $C_1$-$C_{20}$ alkoxy, $C_2$-$C_{20}$ alkenyloxy, $C_2$-$C_{20}$ alkynyloxy, $C_6$-$C_{20}$ aryloxy, $C_2$-$C_{20}$ alkoxycarbonyl, $C_1$-$C_{20}$ alkylthio, $C_1$-$C_{20}$ alkylsulfonyl, or $C_1$-$C_{20}$ alkylsulfinyl, each of which may be further substituted with $C_1$-$C_6$ alkyl, halide, $C_1$-$C_6$ alkoxy or with a phenyl group optionally substituted with halide, $C_1$-$C_6$ alkyl, or $C_1$-$C_6$ alkoxy. More preferably, in compounds of this type, X, $L^1$, and $L^2$ are taken together to be cyclopentadienyl or indenyl, each optionally substituted with vinyl, $C_1$-$C_{10}$ alkyl, $C_5$-$C_{20}$ aryl, $C_1$-$C_{10}$ carboxylate, $C_2$-$C_{10}$ alkoxycarbonyl, $C_1$-$C_{10}$ alkoxy, or $C_5$-$C_{20}$ aryloxy, each optionally substituted with $C_1$-$C_6$ alkyl, halide, $C_1$-$C_6$ alkoxy or with a phenyl group optionally substituted with halide, $C_1$-$C_6$ alkyl or $C_1$-$C_6$ alkoxy. Most preferably, X, $L^1$ and $L^2$ may be taken together to be cyclopentadienyl, optionally substituted with vinyl, hydrogen, methyl, or phenyl. Tetradentate ligands include, but are not limited to O$_2$C(CH$_2$)$_2$P(Ph)(CH$_2$)$_2$P(Ph)(CH$_2$)$_2$CO$_2$, phthalocyanines, and porphyrins.

Complexes wherein $L^2$ and $R^2$ are linked are examples of the fourth group of catalysts, and are commonly called "Grubbs-Hoveyda" catalysts. Examples of Grubbs-Hoveyda-type catalysts include the following:

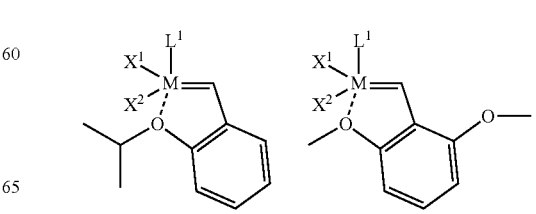

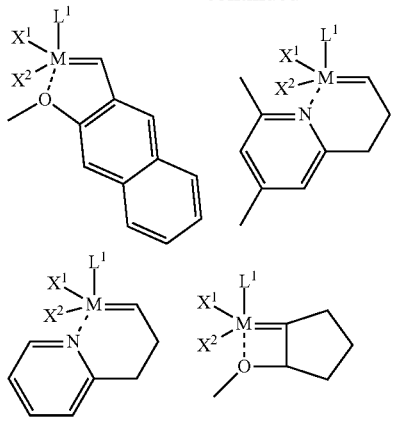

wherein $L^1$, $X^1$, $X^2$, and M are as described for any of the other groups of catalysts.

In addition to the catalysts that have the structure of formula (III), as described above, other transition metal carbene complexes include, but are not limited to:

neutral ruthenium or osmium metal carbene complexes containing metal centers that are formally in the +2 oxidation state, have an electron count of 16, are penta-coordinated, and are of the general formula (IX);

neutral ruthenium or osmium metal carbene complexes containing metal centers that are formally in the +2 oxidation state, have an electron count of 18, are hexa-coordinated, and are of the general formula (X);

cationic ruthenium or osmium metal carbene complexes containing metal centers that are formally in the +2 oxidation state, have an electron count of 14, are tetra-coordinated, and are of the general formula (XI); and cationic ruthenium or osmium metal carbene complexes containing metal centers that are formally in the +2 oxidation state, have an electron count of 14, are tetra-coordinated, and are of the general formula (XII)

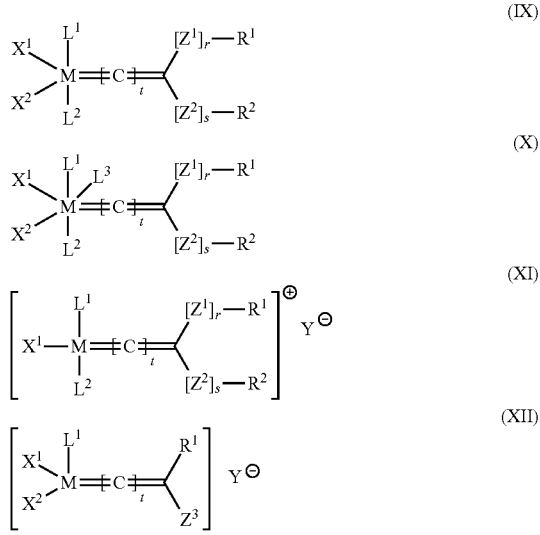

wherein: $X^1$, $X^2$, $L^1$, $L^2$, n, $L^3$, $R^1$, and $R^2$ are as defined for any of the previously defined four groups of catalysts; r and s are independently zero or 1; t is an integer in the range of zero to 5;

Y is any non-coordinating anion (e.g., a halide ion, $BF_4^-$, etc.); $Z^1$ and $Z^2$ are independently selected from —O—, —S—, —$NR^2$—, —$PR^2$—, —P(=O)$R^2$—, —P(O$R^2$)—, —P(=O)(O$R^2$)—, —C(=O)—, —C(=O)O—, —OC(=O)—, —OC(=O)O—, —S(=O)—, and —S(=O)$_2$—; $Z^3$ is any cationic moiety such as —P($R^2$)$_3^+$ or —N($R^2$)$_3^+$; and any two or more of $X^1$, $X^2$, $L^1$, $L^2$, $L^3$, n, $Z^1$, $Z^2$, $Z^3$, $R^1$, and $R^2$ may be taken together to form a cyclic group, e.g., a multidentate ligand, and wherein any one or more of $X^1$, $X^2$, $L^1$, $L^2$, n, $L^3$, $Z^1$, $Z^2$, $Z^3$, $R^1$, and $R^2$ may be attached to a support.

Other suitable complexes include Group 8 transition metal carbenes bearing a cationic substituent, such as are disclosed in U.S. Pat. No. 7,365,140 (Piers et al.) having the general structure (XIII):

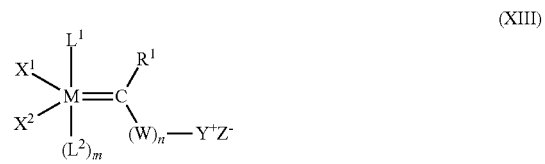

wherein:

M is a Group 8 transition metal;

$L^1$ and $L^2$ are neutral electron donor ligands;

$X^1$ and $X^2$ are anionic ligands;

$R^1$ is hydrogen, $C_1$-$C_{12}$ hydrocarbyl, or substituted $C_1$-$C_{12}$ hydrocarbyl;

W is an optionally substituted and/or heteroatom-containing $C_1$-$C_{20}$ hydrocarbylene linkage;

Y is a positively charged Group 15 or Group 16 element substituted with hydrogen, $C_1$-$C_{12}$ hydrocarbyl, substituted $C_1$-$C_{12}$ hydrocarbyl; heteroatom-containing $C_1$-$C_{12}$ hydrocarbyl, or substituted heteroatom-containing hydrocarbyl;

$Z^-$ is a negatively charged counterion;

m is zero or 1; and n is zero or 1;

wherein any two or more of $L^1$, $L^2$, $X^1$, $X^2$, $R^1$, W, and Y can be taken together to form a cyclic group.

Each of M, $L^1$, $L^2$, $X^1$, and $X^2$ in structure (XIII) may be as previously defined herein.

W is an optionally substituted and/or heteroatom-containing $C_1$-$C_{20}$ hydrocarbylene linkage, typically an optionally substituted $C_1$-$C_{12}$ alkylene linkage, e.g., —(CH$_2$)$_i$— where i is an integer in the range of 1 to 12 inclusive and any of the hydrogen atoms may be replaced with a non-hydrogen substituent as described earlier herein with regard to the definition of the term "substituted." The subscript n is zero or 1, meaning that W may or may not be present. In a preferred embodiment, n is zero.

Y is a positively charged Group 15 or Group 16 element substituted with hydrogen, $C_1$-$C_{12}$ hydrocarbyl, substituted $C_1$-$C_{12}$ hydrocarbyl, heteroatom-containing $C_1$-$C_{12}$ hydrocarbyl, or substituted heteroatom-containing hydrocarbyl. Preferably, Y is a $C_1$-$C_{12}$ hydrocarbyl-substituted, positively charged Group 15 or Group 16 element. Representative Y groups include P($R^2$)$_3$, P($R^2$)$_3$, As($R^2$)$_3$, S($R^2$)$_2$, O($R^2$)$_2$, where the $R^2$ are independently selected from $C_1$-$C_{12}$ hydrocarbyl; within these, preferred Y groups are phosphines of the structure P($R^2$)$_3$ wherein the $R^2$ are independently selected from $C_1$-$C_{12}$ alkyl and aryl, and thus include, for example, methyl, ethyl, n-propyl, isopropyl, n-butyl, isobutyl, t-butyl, cyclopentyl, cyclohexyl, and phenyl. Y can also be a heterocyclic group containing the positively charged Group 15 or Group 16 element. For instance, when the Group 15 or Group 16 element is nitrogen, Y may be an optionally substituted pyridinyl, pyrazinyl, or imidazolyl group.

$Z^-$ is a negatively charged counterion associated with the cationic complex, and may be virtually any anion, so long as the anion is inert with respect to the components of the complex and the reactants and reagents used in the metathesis reaction catalyzed. Preferred $Z^-$ moieties are weakly coordinating anions, such as, for instance, $[B(C_6F_5)_4]^-$, $[BF_4]^-$, $[B(C_6N_4)]^-$, $[CF_3S(O)_3]^-$, $[PF_6]^-$, $[SbF_6]^-$, $[AlCl_4]^-$, $[FSO_3]^-$, $[CB_{11}H_6Cl_6]^-$, $[CB_{11}H_6Br_6]^-$, and $[SO_3F:SbF_5]^-$. Preferred anions suitable as $Z^-$ are of the formula $B(R^{15})_4^-$ where $R^{15}$ is fluoro, aryl, or perfluorinated aryl, typically fluoro or perfluorinated aryl. Most preferred anions suitable as $Z^-$ are $BF_4^-$ and $B(C_6F_5)^-$, optimally the latter.

It should be emphasized that any two or more of $X^1$, $X^2$, $L^1$, $L^2$, $R^1$, W, and Y can be taken together to form a cyclic group, as disclosed, for example, in U.S. Pat. No. 5,312,940 to Grubbs et al. When any of $X^1$, $X^2$, $L^1$, $L^2$, $R^1$, W, and Y are linked to form cyclic groups, those cyclic groups may be five- or six-membered rings, or may comprise two or three five- or six-membered rings, which may be either fused or linked. The cyclic groups may be aliphatic or aromatic, and may be heteroatom-containing and/or substituted, as explained in part (I) of this section.

One group of exemplary catalysts encompassed by the structure of formula (XIII) are those wherein m and n are zero, such that the complex has the structure of formula (XIV)

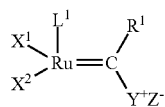

(XIV)

Possible and preferred $X^1$, $X^2$, and $L^1$ ligands are as described earlier with respect to complexes of formula (I), as are possible and preferred $Y^+$ and $Z^-$ moieties. M is Ru or Os, preferably Ru, and $R^1$ is hydrogen or $C_1$-$C_{12}$ alkyl, preferably hydrogen.

In formula (XIV)-type catalysts, $L^1$ is preferably a heteroatom-containing carbene ligand having the structure of formula (XV)

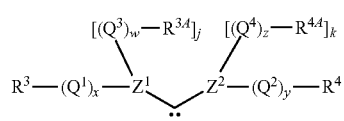

(XV)

such that complex (XIV) has the structure of formula (XVI)

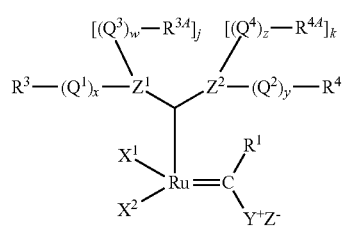

(XVI)

wherein $X^1$, $X^2$, $R^1$, $R^2$, Y, and Z are as defined previously, and the remaining substituents are as follows:

$Z^1$ and $Z^2$ are heteroatoms typically selected from N, O, S, and P. Since O and S are divalent, j is necessarily zero when $Z^1$ is O or S, and k is necessarily zero when $Z^2$ is O or S. However, when $Z^1$ is N or P, then j is 1, and when $Z^2$ is N or P, then k is 1. In a preferred embodiment, both $Z^1$ and $Z^2$ are N.

$Q^1$, $Q^2$, $Q^3$, and $Q^4$ are linkers, e.g., $C_1$-$C_{12}$ hydrocarbylene, substituted $C_1$-$C_{12}$ hydrocarbylene, heteroatom-containing $C_1$-$C_{12}$ hydrocarbylene, substituted heteroatom-containing $C_1$-$C_{12}$ hydrocarbylene, or —(CO)—, and w, x, y, and z are independently zero or 1, meaning that each linker is optional. Preferably, w, x, y, and z are all zero.

$R^3$, $R^{3A}$, $R^4$, and $R^{4A}$ are independently selected from hydrogen, hydrogen, $C_1$-$C_{20}$ hydrocarbyl, substituted $C_1$-$C_{20}$ hydrocarbyl, heteroatom-containing hydrocarbyl, and substituted heteroatom-containing $C_1$-$C_{20}$ hydrocarbyl.

Preferably, w, x, y, and z are zero, $Z^1$ and $Z^1$ are N, and $R^{3A}$ and $R^{4A}$ are linked to form -Q-, such that the complex has the structure of formula (XVII)

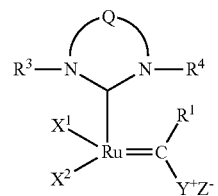

(XVII)

wherein $R^3$ and $R^4$ are defined above, with preferably at least one of $R^3$ and $R^4$, and more preferably both $R^3$ and $R^4$, being alicyclic or aromatic of one to about five rings, and optionally containing one or more heteroatoms and/or substituents. Q is a linker, typically a hydrocarbylene linker, including $C_1$-$C_{12}$ hydrocarbylene, substituted $C_1$-$C_{12}$ hydrocarbylene, heteroatom-containing $C_1$-$C_{12}$ hydrocarbylene, or substituted heteroatom-containing $C_1$-$C_{12}$ hydrocarbylene linker, wherein two or more substituents on adjacent atoms within Q may be linked to form an additional cyclic structure, which may be similarly substituted to provide a fused polycyclic structure of two to about five cyclic groups. Q is often, although not necessarily, a two-atom linkage or a three-atom linkage, e.g., —CH₂—CH₂—, —CH(Ph)—CH(Ph)— where Ph is phenyl; =CR—N=, giving rise to an unsubstituted (when R=H) or substituted (R=other than H) triazolyl group; or —CH₂—SiR₂—CH₂— (where R is H, alkyl, alkoxy, etc.).

In a more preferred embodiment, Q is a two-atom linkage having the structure —CR⁸R⁹—CR¹⁰R¹¹— or —CR⁸=CR¹⁰—, preferably —CR⁸R⁹—CR¹⁰R¹¹—, wherein $R^8$, $R^9$, $R^{10}$, and $R^{11}$ are independently selected from hydrogen, $C_1$-$C_{12}$ hydrocarbyl, substituted $C_1$-$C_{12}$ hydrocarbyl, heteroatom-containing $C_1$-$C_{12}$ hydrocarbyl, substituted heteroatom-containing $C_1$-$C_{12}$ hydrocarbyl, and functional groups as defined in part (I) of this section. Examples of functional groups here include carboxyl, $C_1$-$C_{20}$ alkoxy, $C_5$-$C_{20}$ aryloxy, $C_2$-$C_{20}$ alkoxycarbonyl, $C_2$-$C_{20}$ alkoxycarbonyl, $C_2$-$C_{20}$ acyloxy, $C_1$-$C_{20}$ alkylthio, $C_5$-$C_{20}$ arylthio, $C_1$-$C_{20}$ alkylsulfonyl, and $C_1$-$C_{20}$ alkylsulfinyl, optionally substituted with one or more moieties selected from $C_1$-$C_{10}$ alkyl, $C_1$-$C_{10}$ alkoxy, $C_5$-$C_{20}$ aryl, hydroxyl, sulfhydryl, formyl, and halide. Alternatively, any two of $R^8$, $R^9$, $R^{10}$, and $R^{11}$ may be linked together to form a substituted or unsubstituted, saturated or unsaturated ring structure, e.g., a $C_4$-$C_{12}$ alicyclic group or a $C_5$ or $C_6$ aryl group, which may itself be substituted, e.g., with linked or fused alicyclic or aromatic groups, or with other substituents.

Further details concerning such formula (XIII) complexes, as well as associated preparation methods, may be obtained from U.S. Pat. No. 7,365,140, herein incorporated by reference.

As is understood in the field of catalysis, suitable solid supports for any of the catalysts described herein may be of synthetic, semi-synthetic, or naturally occurring materials, which may be organic or inorganic, e.g., polymeric, ceramic, or metallic. Attachment to the support will generally, although not necessarily, be covalent, and the covalent linkage may be direct or indirect, if indirect, typically through a functional group on a support surface.

Non-limiting examples of catalysts that may be used in the reactions of the disclosure include the following, some of which for convenience are identified throughout this disclosure by reference to their molecular weight:

12

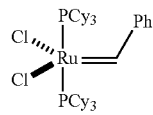

14

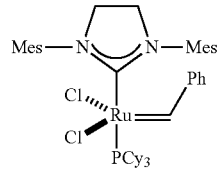

16

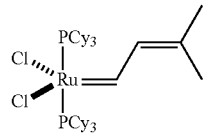

18

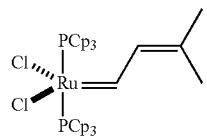

20

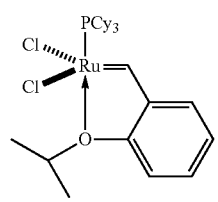

22

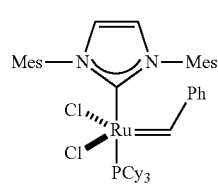

24

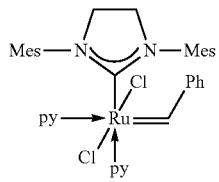

26

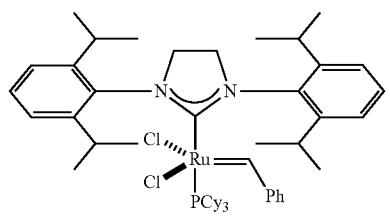

28

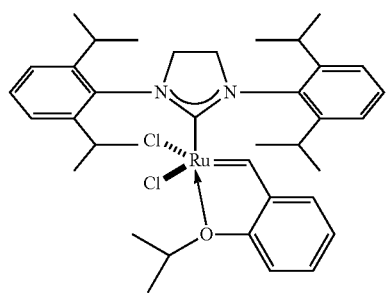

50

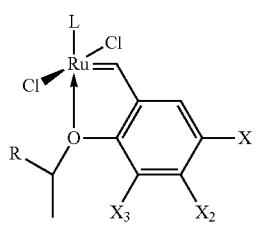

where
L = PCy$_3$, siMes, Mes, Phobane
X = H, NO$_2$, SO$_2$N(CH$_3$)$_2$
X$_2$ = H, N$^+$(C$_2$H$_3$)$_2$CH$_3$
X$_3$ = H, Phenyl
R = H, alkyl, aryl, CO$_2$Me

52

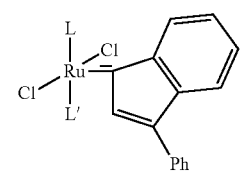

where
L = PCy$_3$, siMes, Mes, Phobane
L' = PCy$_3$, Phobane

SiMes

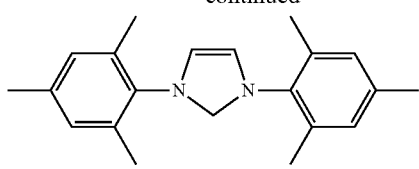
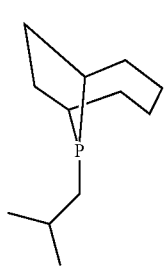
Phobane
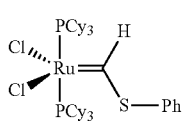
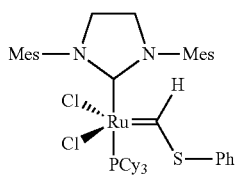
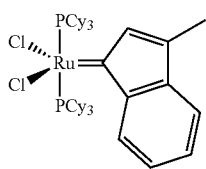
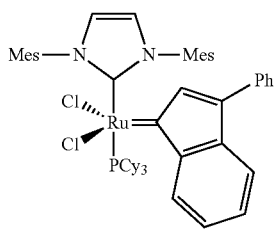
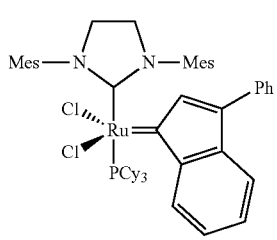
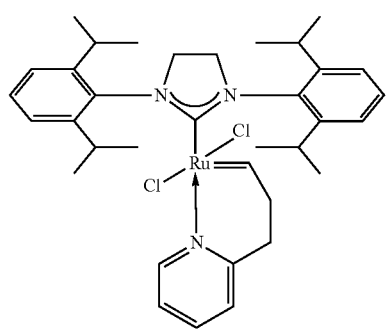
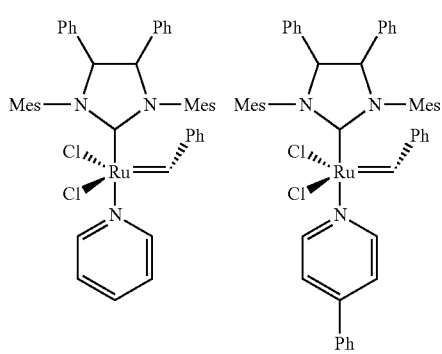
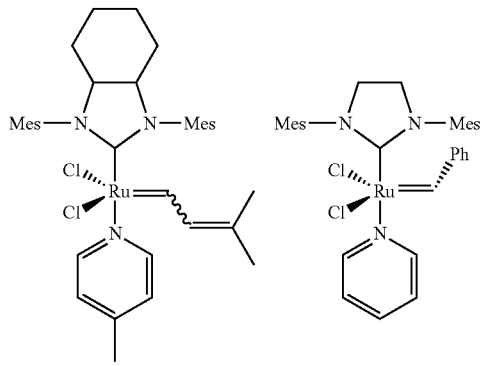
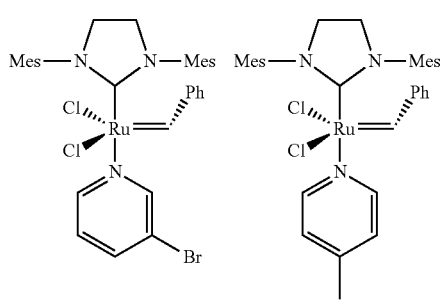
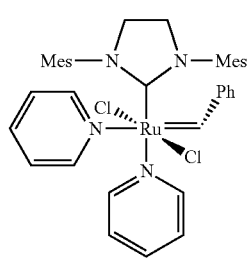

-continued
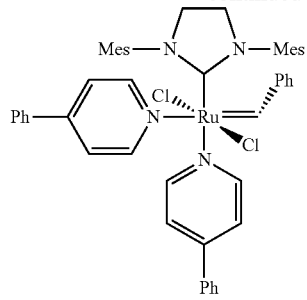
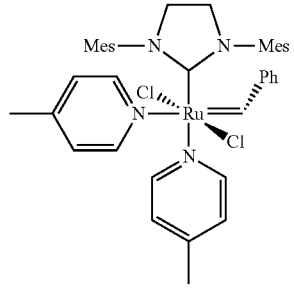
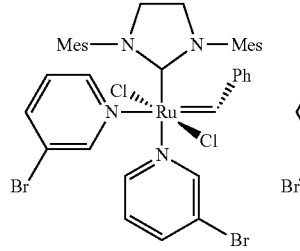
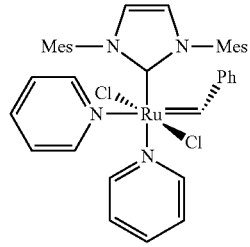
C827
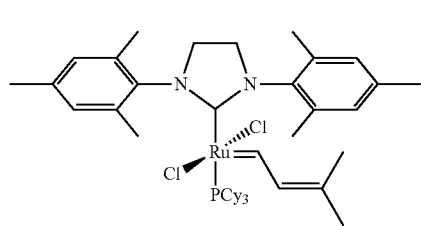
C859
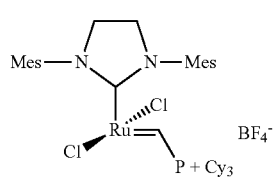
C841-n
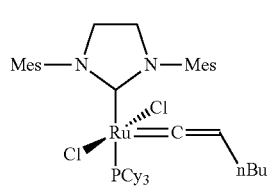
-continued
C916
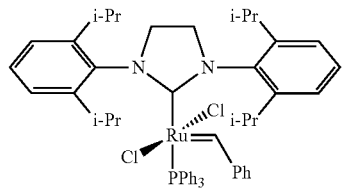
C965-p
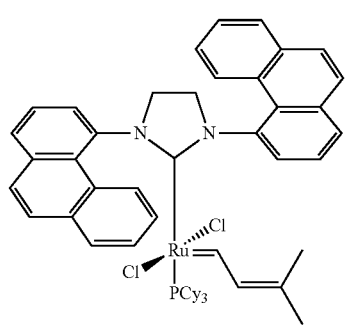
C727
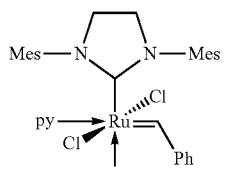
C577
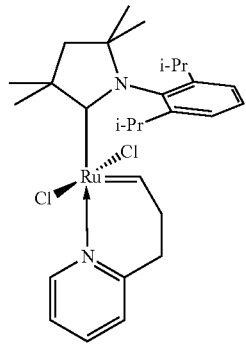
C646
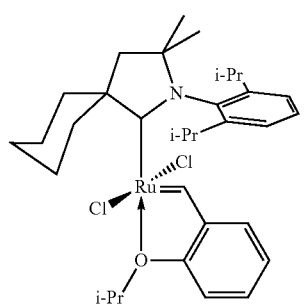
C701
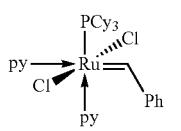

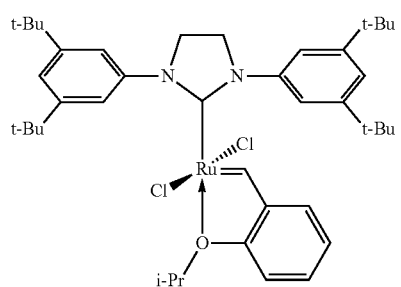
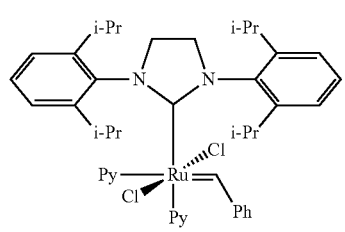
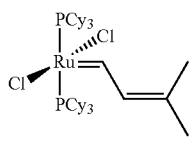
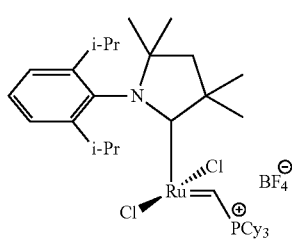
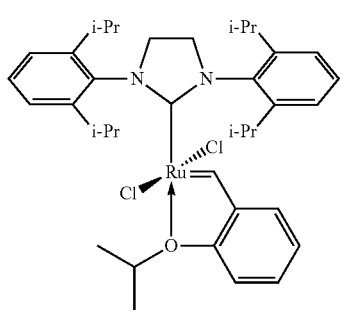
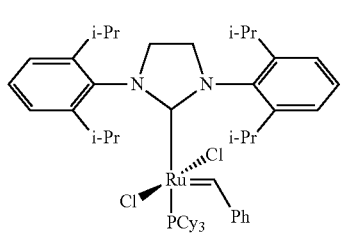
C767-m
C811
C801
C838
C712
C933
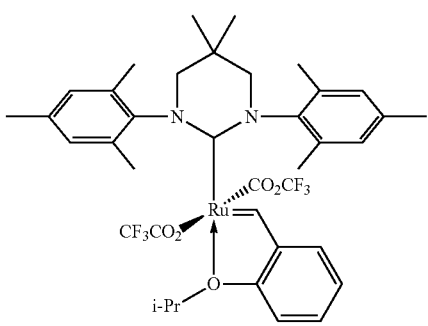
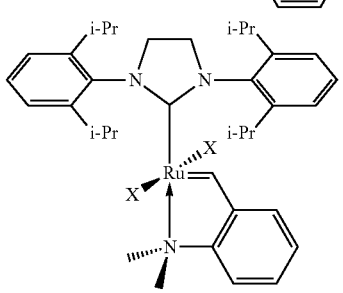
C697 (X = Cl)
C785 (X = Br)
C879 (X = I)
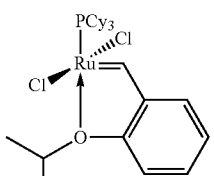
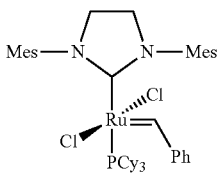
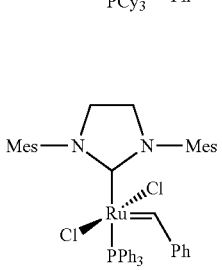
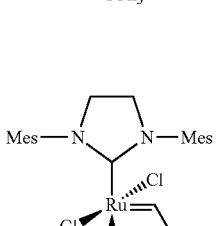
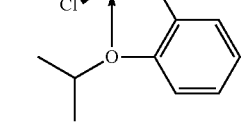
C824
C601
C848
C831
C627

-continued
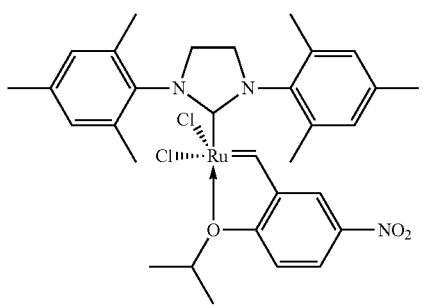
C672
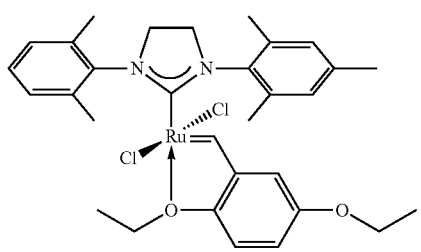
C657
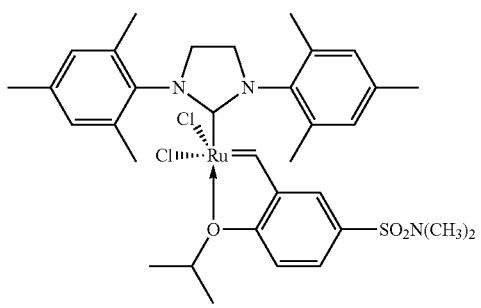
C734
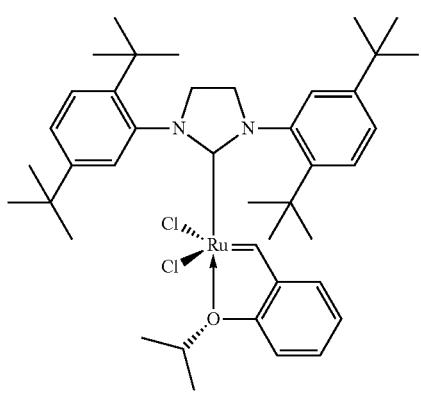
C767
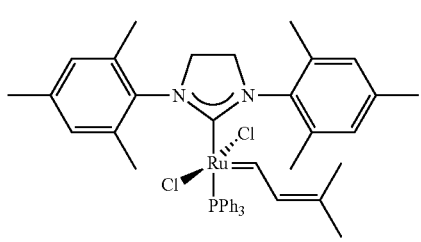
C809
-continued
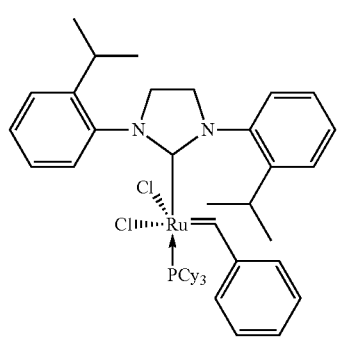
C849
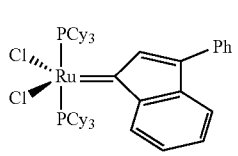
C923
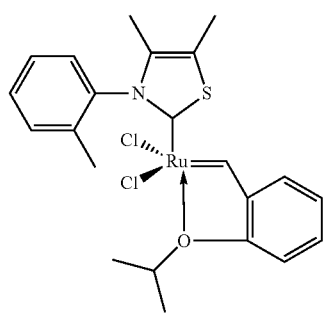
C-524
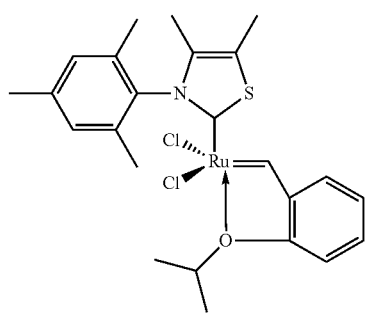
C-552
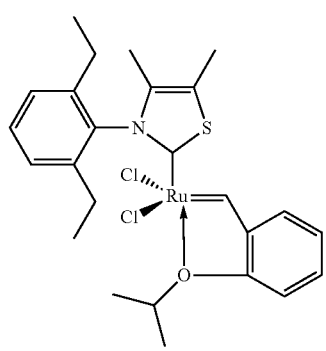
C-556

DPAI-278
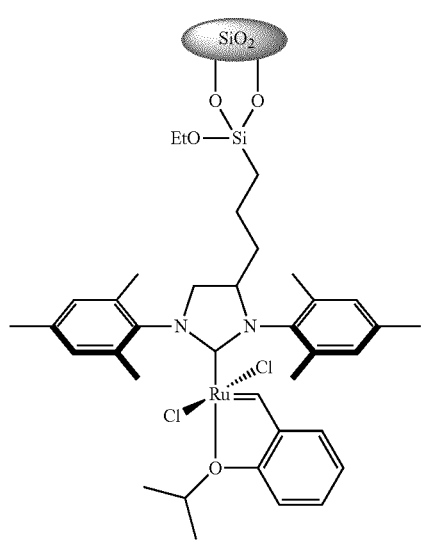
C-598
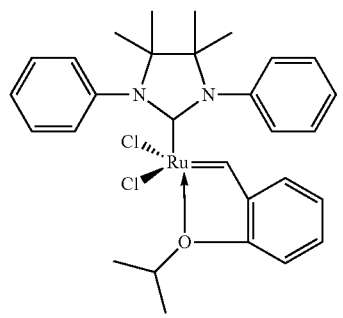
C-626
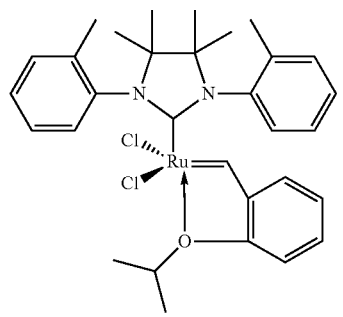
C949
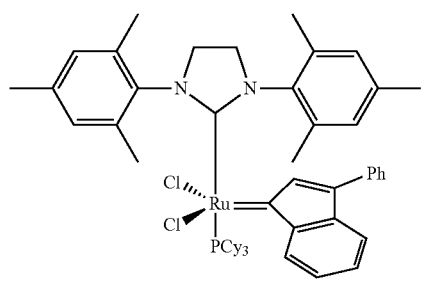
C823
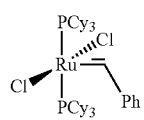
C606
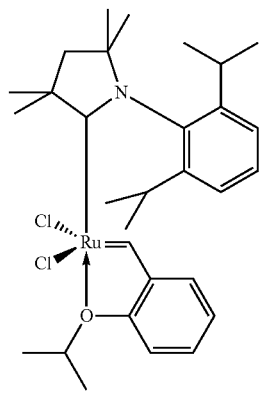
C629
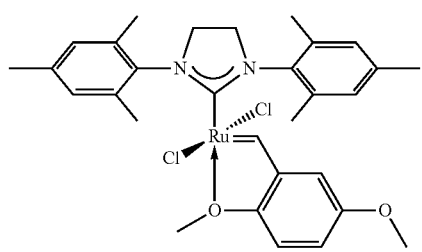
C833
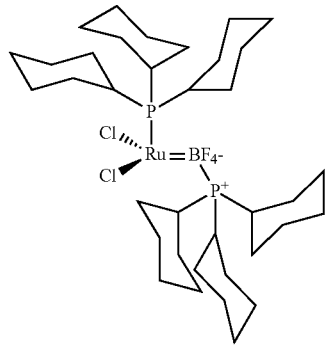
C613
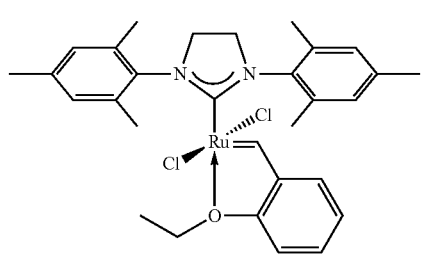
C827
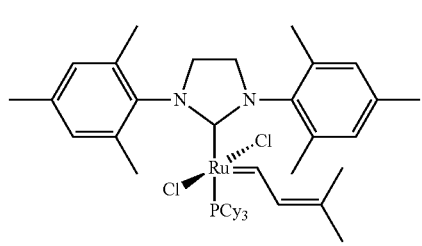

C627
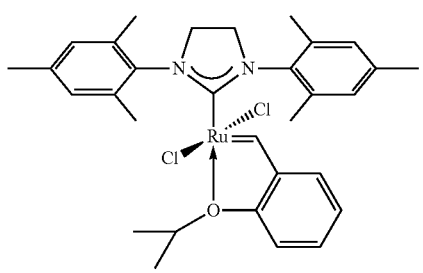
C793
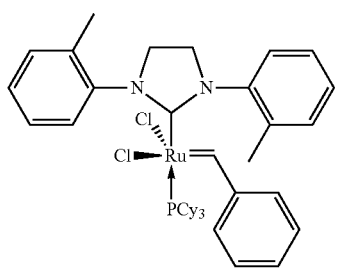
C598Cs
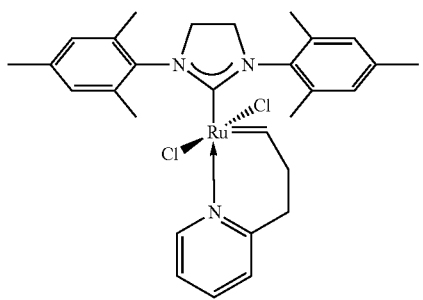
C782
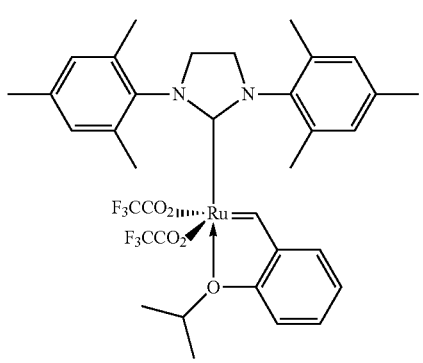
C702
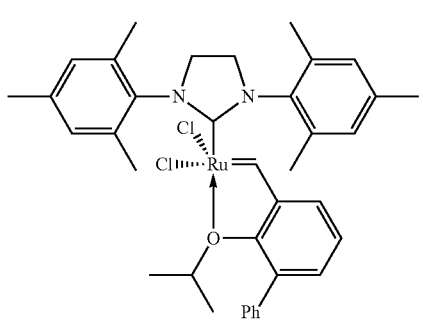
C884
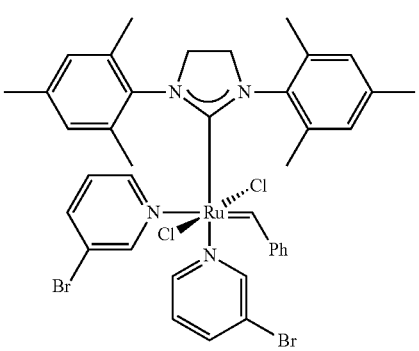
C933
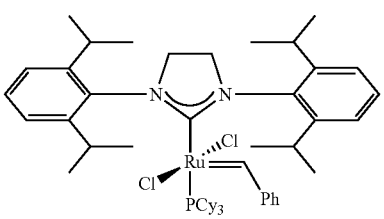
C866
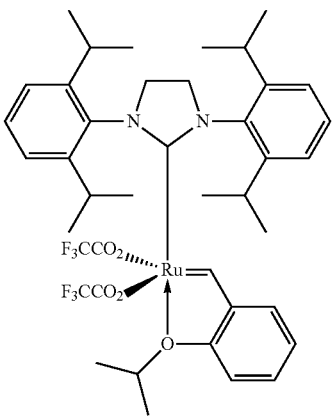
C571
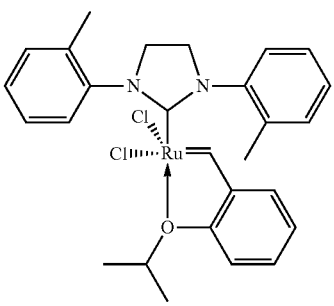

-continued

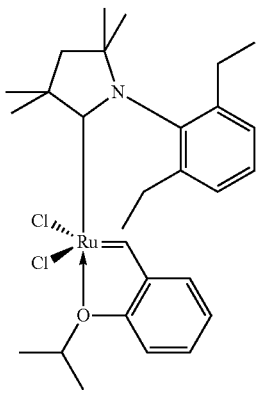

C578

In the foregoing molecular structures and formulae, Ph represents phenyl, Cy represents cyclohexane, Me represents methyl, nBu represents n-butyl, i-Pr represents isopropyl, py represents pyridine (coordinated through the N atom), and Mes represents mesityl (i.e., 2,4,6-trimethylphenyl).

Further examples of catalysts useful in the reactions of the present disclosure include the following: ruthenium (II) dichloro(3-methyl-1,2-butenylidene)bis(tricyclopentylphosphine) (C716); ruthenium (II) dichloro(3-methyl-1,2-butenylidene)bis(tricyclohexylphosphine) (C801); ruthenium (II) dichloro(phenylmethylene)bis(tricyclohexylphosphine) (C823); ruthenium (II) [1,3-bis-(2,4,6-trimethylphenyl)-2-imidazolidinylidene)dichloro(phenylmethylene) (triphenylphosphine) (C830), and ruthenium (II) dichloro(vinyl phenylmethylene)bis(tricyclohexylphosphine) (C835); ruthenium (II) dichloro(tricyclohexylphosphine) (o-isopropoxyphenylmethylene) (C601), and ruthenium (II) (1,3-bis-(2,4,6,-trimethylphenyl)-2-imidazolidinylidene)dichloro (phenylmethylene) (bis 3-bromopyridine (C884)).

Exemplary ruthenium-based metathesis catalysts include those represented by structures 12 (commonly known as Grubbs's catalyst), 14 and 16. Structures 18, 20, 22, 24, 26, 28, 60, 62, 64, 66, and 68 represent additional ruthenium-based metathesis catalysts. Catalysts C627, C682, C697, C712, and C827 represent still additional ruthenium-based catalysts. General structures 50 and 52 represent additional ruthenium-based metathesis catalysts of the type reported in *Chemical & Engineering News*; Feb. 12, 2007, at pages 37-47. In the structures, Ph is phenyl, Mes is mesityl, py is pyridine, Cp is cyclopentyl, and Cy is cyclohexyl.

Techniques for using the metathesis catalysts are known in the art (see, for example, U.S. Pat. Nos. 7,102,047; 6,794,534; 6,696,597; 6,414,097; 6,306,988; 5,922,863; 5,750,815; and metathesis catalysts with ligands in U.S. Publication No. 2007/0004917 A1), all incorporated by reference herein in their entireties. A number of the metathesis catalysts as shown are manufactured by Materia, Inc. (Pasadena, Calif.).

Additional exemplary metathesis catalysts include, without limitation, metal carbene complexes selected from the group consisting of molybdenum, osmium, chromium, rhenium, and tungsten. The term "complex" refers to a metal atom, such as a transition metal atom, with at least one ligand or complexing agent coordinated or bound thereto. Such a ligand typically is a Lewis base in metal carbene complexes useful for alkyne- or alkene-metathesis. Typical examples of such ligands include phosphines, halides and stabilized carbenes. Some metathesis catalysts may employ plural metals or metal co-catalysts (e.g., a catalyst comprising a tungsten halide, a tetraalkyl tin compound, and an organoaluminum compound).

An immobilized catalyst can be used for the metathesis process. An immobilized catalyst is a system comprising a catalyst and a support, the catalyst associated with the support. Exemplary associations between the catalyst and the support may occur by way of chemical bonds or weak interactions (e.g. hydrogen bonds, donor acceptor interactions) between the catalyst, or any portions thereof, and the support or any portions thereof. Support is intended to include any material suitable to support the catalyst. Typically, immobilized catalysts are solid phase catalysts that act on liquid or gas phase reactants and products. Exemplary supports are polymers, silica or alumina. Such an immobilized catalyst may be used in a flow process. An immobilized catalyst can simplify purification of products and recovery of the catalyst so that recycling the catalyst may be more convenient.

The metathesis process can be conducted under any conditions adequate to produce the desired metathesis products. For example, stoichiometry, atmosphere, solvent, temperature and pressure can be selected to produce a desired product and to minimize undesirable byproducts. The metathesis process may be conducted under an inert atmosphere. Similarly, if a reagent is supplied as a gas, an inert gaseous diluent can be used. The inert atmosphere or inert gaseous diluent typically is an inert gas, meaning that the gas does not interact with the metathesis catalyst to substantially impede catalysis. For example, particular inert gases are selected from the group consisting of helium, neon, argon, nitrogen and combinations thereof.

Similarly, if a solvent is used, the solvent chosen may be selected to be substantially inert with respect to the metathesis catalyst. For example, substantially inert solvents include, without limitation, aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc.

In certain embodiments, a ligand may be added to the metathesis reaction mixture. In many embodiments using a ligand, the ligand is selected to be a molecule that stabilizes the catalyst, and may thus provide an increased turnover number for the catalyst. In some cases the ligand can alter reaction selectivity and product distribution. Examples of ligands that can be used include Lewis base ligands, such as, without limitation, trialkylphosphines, for example tricyclohexylphosphine and tributyl phosphine; triarylphosphines, such as triphenylphosphine; diarylalkylphosphines, such as, diphenylcyclohexylphosphine; pyridines, such as 2,6-dimethylpyridine, 2,4,6-trimethylpyridine; as well as other Lewis basic ligands, such as phosphine oxides and phosphinites. Additives also may be present during metathesis that increase catalyst lifetime.

The metathesis reaction temperature may be a rate-controlling variable where the temperature is selected to provide a desired product at an acceptable rate. The metathesis temperature may be greater than −40° C., may be greater than about −20° C., and is typically greater than about 0° C. or greater than about 20° C. Typically, the metathesis reaction temperature is less than about 150° C., typically less than about 120° C. An exemplary temperature range for the metathesis reaction ranges from about 20° C. to about 120° C.

The metathesis reaction can be run under any desired pressure. Typically, it will be desirable to maintain a total pressure that is high enough to keep the cross-metathesis reagent in solution. Therefore, as the molecular weight of the cross-metathesis reagent increases, the lower pressure range typically decreases since the boiling point of the cross-metathesis reagent increases. The total pressure may be selected to be greater than about 10 kPa, in some embodiments greater than about 30 kPa, or greater than about 100 kPa. Typically, the reaction pressure is no more than about 7000 kPa, in some embodiments no more than about 3000 kPa. An exemplary pressure range for the metathesis reaction is from about 100 kPa to about 3000 kPa.

In some embodiments, the metathesis reaction is catalyzed by a system containing both a transition and a non-transition metal component. The most active and largest number of catalyst systems are derived from Group VI A transition metals, for example, tungsten and molybdenum.

In some embodiments, the unsaturated polyol ester is partially hydrogenated before it is subjected to the metathesis reaction. Partial hydrogenation of the unsaturated polyol ester reduces the number of double bonds that are available for in the subsequent metathesis reaction. In some embodiments, the unsaturated polyol ester is metathesized to form a metathesized unsaturated polyol ester, and the metathesized unsaturated polyol ester is then hydrogenated (e.g., partially or fully hydrogenated) to form a hydrogenated metathesized unsaturated polyol ester.

Hydrogenation may be conducted according to any known method for hydrogenating double bond-containing compounds such as vegetable oils. In some embodiments, the unsaturated polyol ester or metathesized unsaturated polyol ester is hydrogenated in the presence of a nickel catalyst that has been chemically reduced with hydrogen to an active state. Commercial examples of supported nickel hydrogenation catalysts include those available under the trade designations "NYSOFACT", "NYSOSEL", and "NI 5248 D" (from Englehard Corporation, Iselin, N.H.). Additional supported nickel hydrogenation catalysts include those commercially available under the trade designations "PRICAT 9910", "PRICAT 9920", "PRICAT 9908", "PRICAT 9936" (from Johnson Matthey Catalysts, Ward Hill, Mass.).

The hydrogenation catalyst may comprise, for example, nickel, copper, palladium, platinum, molybdenum, iron, ruthenium, osmium, rhodium, or iridium. Combinations of metals also may be used. Useful catalyst may be heterogeneous or homogeneous. In some embodiments, the catalysts are supported nickel or sponge nickel type catalysts.

In some embodiments, the hydrogenation catalyst comprises nickel that has been chemically reduced with hydrogen to an active state (i.e., reduced nickel) provided on a support. The support may comprise porous silica (e.g., kieselguhr, infusorial, diatomaceous, or siliceous earth) or alumina. The catalysts are characterized by a high nickel surface area per gram of nickel.

The particles of supported nickel catalyst may be dispersed in a protective medium comprising hardened triacylglyceride, edible oil, or tallow. In an exemplary embodiment, the supported nickel catalyst is dispersed in the protective medium at a level of about 22 weight % nickel.

The supported nickel catalysts may be of the type described in U.S. Pat. No. 3,351,566 (Taylor et al.), and incorporated by reference herein. These catalysts comprise solid nickel-silica having a stabilized high nickel surface area of 45 to 60 sq. meters per gram and a total surface area of 225 to 300 sq. meters per, gram. The catalysts are prepared by precipitating the nickel and silicate ions from solution such as nickel hydrosilicate onto porous silica particles in such proportions that the activated catalyst contains 25 weight % to 50 weight % nickel and a total silica content of 30 weight % to 90 weight %. The particles are activated by calcining in air at 600° F. to 900° F., then reducing with hydrogen.

Useful catalysts having a high nickel content are described in EP 0 168 091 (incorporated by reference herein), wherein the catalyst is made by precipitation of a nickel compound. A soluble aluminum compound is added to the slurry of the precipitated nickel compound while the precipitate is maturing. After reduction of the resultant catalyst precursor, the reduced catalyst typically has a nickel surface area of the order of 90 to 150 sq. m per gram of total nickel. The catalysts have a nickel/aluminum atomic ratio in the range of 2 to 10 and have a total nickel content of more than about 66 weight %.

Useful high activity nickel/alumina/silica catalysts are described in EP 167,201. The reduced catalysts have a high nickel surface area per gram of total nickel in the catalyst. Useful nickel/silica hydrogenation catalysts are described in U.S. Pat. No. 6,846,772. The catalysts are produced by heating a slurry of particulate silica (e.g. kieselguhr) in an aqueous nickel amine carbonate solution for a total period of at least 200 minutes at a pH above 7.5, followed by filtration, washing, drying, and optionally calcination. The nickel/silica hydrogenation catalysts are reported to have improved filtration properties. U.S. Pat. No. 4,490,480 reports high surface area nickel/alumina hydrogenation catalysts having a total nickel content of 5% to 40% weight.

Commercial examples of supported nickel hydrogenation catalysts include those available under the trade designations "NYSOFACT", "NYSOSEL", and "NI 5248 D" (from Englehard Corporation, Iselin, N.H.). Additional supported nickel hydrogenation catalysts include those commercially available under the trade designations "PRICAT 9910", "PRICAT 9920", "PRICAT 9908", "PRICAT 9936" (from Johnson Matthey Catalysts, Ward Hill, Mass.).

Hydrogenation may be carried out in a batch or in a continuous process and may be partial hydrogenation or complete hydrogenation. In a representative batch process, a vacuum is pulled on the headspace of a stirred reaction vessel and the reaction vessel is charged with the material to be hydrogenated (e.g., RBD soybean oil or metathesized RBD soybean oil). The material is then heated to a desired temperature. Typically, the temperature ranges from about 50° C. to 350° C., for example, about 100° C. to 300° C. or about 150° C. to 250° C. The desired temperature may vary, for example, with hydrogen gas pressure. Typically, a higher gas pressure will require a lower temperature. In a separate container, the hydrogenation catalyst is weighed into a mixing vessel and is slurried in a small amount of the material to be hydrogenated (e.g., RBD soybean oil or metathesized RBD soybean oil). When the material to be hydrogenated reaches the desired temperature, the slurry of hydrogenation catalyst is added to the reaction vessel. Hydrogen gas is then pumped into the reaction vessel to achieve a desired pressure of $H_2$ gas. Typically, the $H_2$ gas pressure ranges from about 15 to 3000 psig, for example, about 15 psig to 90 psig. As the gas pressure increases, more specialized high-pressure processing equipment may be required. Under these conditions the hydrogenation reaction begins and the temperature is allowed to increase to the desired hydrogenation temperature (e.g., about 120° C. to 200° C.) where it is maintained by cooling the reaction mass, for example, with cooling coils. When the desired degree of hydrogenation is reached, the reaction mass is cooled to the desired filtration temperature.

The amount of hydrogenation catalyst is typically selected in view of a number of factors including, for example, the type of hydrogenation catalyst used, the amount of hydrogenation catalyst used, the degree of unsaturation in the material to be hydrogenated, the desired rate of hydrogenation, the desired degree of hydrogenation (e.g., as measure by iodine value (IV)), the purity of the reagent, and the $H_2$ gas pressure. In some embodiments, the hydrogenation catalyst is used in an amount of about 10 weight % or less, for example, about 5 weight % or less or about 1 weight % or less.

After hydrogenation, the hydrogenation catalyst may be removed from the hydrogenated product using known techniques, for example, by filtration. In some embodiments, the hydrogenation catalyst is removed using a plate and frame filter such as those commercially available from Sparkler Filters, Inc., Conroe Tex. In some embodiments, the filtration is performed with the assistance of pressure or a vacuum. In order to improve filtering performance, a filter aid may be used. A filter aid may be added to the metathesized product directly or it may be applied to the filter. Representative examples of filtering aids include diatomaceous earth, silica, alumina, and carbon. Typically, the filtering aid is used in an amount of about 10 weight % or less, for example, about 5 weight % or less or about 1 weight % or less. Other filtering techniques and filtering aids also may be employed to remove the used hydrogenation catalyst. In other embodiments the hydrogenation catalyst is removed using centrifugation followed by decantation of the product.

The invention will now be described with reference to the following non-limiting examples.

EXAMPLES

Example 1

In this example, the natural oil feedstock was chemically treated with sodium bisulfate to diminish the peroxides and additional non-peroxide catalyst poisons. The treatment began by filling a 3-neck 500 mL round bottom flask with 300 g feedstock of Fatty Acid Methyl Ester (FAME). Next, 0.83 wt % sodium bisulfate (JT Baker Lot #X37H17) was dissolved in 30 g of water and added to the feedstock. The feedstock was then stirred in the flask with an agitator. A nitrogen sparge began as the feedstock was heated to 60° C. The feedstock was held at 60° C. for at least 45 minutes to degas. The feedstock remained at 60° C. for an additional 90 minutes. Next, the feedstock was removed from the heating mantel and cooled down to 40° C. at which point the nitrogen sparge was stopped. The treated feedstock was then poured into a separation funnel. Approximately 300 mL of warm water was added to the feedstock. Then, the mixture was shaken vigorously to wash out and separate the treated feedstock from the other components. When the materials separated within the funnel, the water layer was drained from the bottom. The washing step was repeated several times (3 times recommended). A rotovap was then used to dry the top layer. A vacuum was pulled on the rotovap with nitrogen, and then the material was heated to 80° C. The vacuum was held at 80° C. for 1-2 hours. Then, the material was cooled to 30-40° C. before breaking the vacuum with nitrogen. The treated feedstock was then stored in two 125 mL amber bottles and 1 clear jar, where the feedstock was nitrogen sparged, blanketed, capped, and sealed.

The treated feedstock was then purged with argon for 1 hr to remove oxygen. The ruthenium metathesis catalyst 827 in the amount specified in Table 1 was then added to the feedstock, wherein the feedstock underwent a self-metathesis reaction. The resulting mixture was stirred at 70° C. for 2 hr and cooled to room temperature. The percent conversion from feedstock to transesterified products was determined by the GC-analysis of transesterified products, as described below.

A 2 mL glass scintillation vial containing a magnetic stirrer was charged with methathesized SBO (~50 mg) and 2 mL of 1% w/w sodium methozide in methanol. The light yellow heterogeneous mixture was stirred at 60° C. for 1 hr. Towards the end of the hour, the mixture turned a homogeneous orange color. To the esterified products was added 2.0 mL D1-H2O and 2.0 mL ethyl acetate, mixed and the phases separated. The organic phase was diluted with ethyl acetate for GC analysis.

The GC analysis conditions were: [column: HP-5™ (30m× 0.25 mm ID, 0.25 um film thickness)]; 100° C. for 1 min, 10° C./min to 250° C., hold for 12 min.; Rt 12.6 min (Methyl Palmitate); Rt 14.2~14.5 min (Methyl Linolenate, Methyl Linoleate, and Methyl Oleate), Rt 14.7 min (Methyl Stearate).

The degree to which the feedstock has been metathesized is shown in percent conversion. Percent conversion was calculated from the GC chromatogram as 100% minus the sum of methyl palmitate, methyl linolenate (cis and trans isomers), methyl linoleate (cis and trans isomers), methyl oleate (cis and trans isomers) and methyl stearate. Additionally, samples and tests for peroxide value (PV) were run using the American Oil Chemists Society (AOCS) Method Cd 8b-90. The starting and final peroxide values, along with the percent conversion for each sample is shown in Table 1.

TABLE 1

| type of FAME | Lot # | metathesis catalyst 827 (ppm/db) | starting material treatment | Start PV value (meq/kg) | Final PV value (meq/kg) | GC % conversion |
|---|---|---|---|---|---|---|
| Soy | MF-SBF6D22 | 20 | none | 10.5 | — | 70 |
| Soy | MF-SBF6D22 | 10 | none | 10.5 | — | 67 |
| Soy | MF-SBF6D22 | 3 | none | 10.5 | — | 13 |
| Soy | MF-SBF6D22 | 10 | Sodium Bisulfite | 10.5 | 0.9 | 69 |
| Soy | MF-SBF6D22 | 10 | Sodium Bisulfite | 10.5 | 0.9 | 70 |
| Soy | MF-SBF6D22 | 3 | Sodium Bisulfite | 10.5 | 0.9 | 58 |
| Soy | MF-SBF6D22 | 3 | Sodium Bisulfite | 10.5 | 0.9 | 67 |
| Soy | MF-SBF6D22 | 2 | Sodium Bisulfite | 10.5 | 0.9 | 55 |
| Soy | MF-SBF6D22 | 1 | Sodium Bisulfite | 10.5 | 0.9 | 24 |
| Soy | MF-SBF6D22 | 10 | Sodium Bisulfite | 11.2 | 0.38 | 69 |
| Soy | MF-SBF6D22 | 10 | Sodium Bisulfite | 11.2 | 0.38 | 70 |
| Soy | MF-SBF6D22 | 3 | Sodium Bisulfite | 11.2 | 0.38 | 59 |
| Soy | MF-SBF6D22 | 3 | Sodium Bisulfite | 11.2 | 0.38 | 66 |
| Soy | MF-SBF6D22 | 2 | Sodium Bisulfite | 11.2 | 0.38 | 54 |
| Soy | MF-SBF6D22 | 1 | Sodium Bisulfite | 11.2 | 0.38 | 33 |

Table 1 shows the type of improvement that sodium bisulfite treatment can have on a natural oil feedstock in terms of removing catalyst poisons and improving conversion. The experimental data shows that an excessive amount of metathesis catalyst (10 to 20 ppm catalyst per mol of carbon-carbon double bonds in the feedstock, or "ppm/db") may reach a maximum theoretical conversion limit regardless of the catalyst poison level. In this example, self-metathesis of fatty acid methyl esters of soybean oil has an apparent maximum theoretical conversion limit of approximately 70%. As the level of metathesis catalyst is lowered below 10 ppm/db, the untreated feedstock has a lower conversion (i.e. 13% conversion with 3 ppm/db metathesis catalyst) (or 19% conversion of the maximum theoretical conversion limit). On the other hand, the feedstock treated with sodium bisulfite has a much lower peroxide value (<1 meq/kg) and a much improved conversion (59-67% conversion with 3 ppm/db metathesis catalyst). This equates to approximately 84-96% of the maximum theoretical limit. This example demonstrates that catalyst poisons, such as peroxides, affect the metathesis catalyst, and removing as much of the catalyst poisons as possible helps conversion at lower catalyst loadings.

Example 2

In this example, the natural oil feedstock was chemically treated with sodium borohydride to diminish the peroxides and additional non-peroxide catalyst poisons. The treatment began by filling a 3-neck 500 mL round bottom flask with 300 g feedstock of Fatty Acid Methyl Ester (FAME). Next, 0.291 g or 0.379 g sodium bisulfate (Aldrich Lot) was added to the flask, for examples MF-SBF6C06 and MF-SBF6D22, respectively. The feedstock was then stirred in the flask with an agitator. A nitrogen sparge was started as the feedstock was heated to 80° C. The feedstock was held at 80° C. for at least 45 minutes to degas. The feedstock remained at 80° C. for an additional 2 hours. Next, 1.5 wt % magnesium silicate (Magnesol) and 1 wt % Celite were added to the flask. The feedstock was then removed from the heating mantel and cooled down to 40° C. at which point the nitrogen sparge was stopped. The treated feedstock was filtered through #4 paper on a Buchner funnel to separate the adsorbent from the feedstock. Twice more, the feedstock was filtered through a Buchner funnel with #2 filter paper. The treated and filtered feedstock were then stored in two 125 mL amber bottles and 1 clear jar, where the feedstock was nitrogen sparged, blanketed, and sealed.

The treated feedstock is then purged with argon for 1 hr to remove oxygen. The ruthenium metathesis catalyst 827 in the amount specified in Table 7 was then added to the feedstock, wherein the feedstock underwent a self-metathesis reaction. The resulting mixture was stirred at 70° C. for 2 hr and cooled to room temperature. The percent conversion was determined by the GC-analysis as previously described in Example 1. Samples and tests for PV were run using the American Oil Chemists Society (AOCS) Method Cd 8b-90. The starting and final peroxide values, along with the percent conversion for each sample are shown in Table 2.

TABLE 2

| type of FAME | Lot # | metathesis catalyst 827 (ppm/db) | starting material treatment | Start PV value (meq/kg) | Final PV value (meq/kg) | GC % conversion |
| --- | --- | --- | --- | --- | --- | --- |
| Soy | MF-SBF6C06 | 20 | none | 5.5 | — | 71 |
| Soy | MF-SBF6C06 | 13 | none | 5.5 | — | 69 |
| Soy | MF-SBF6C06 | 10 | none | 5.5 | — | 65 |
| Soy | MF-SBF6C06 | 3 | none | 5.5 | — | 8 |
| Soy | MF-SBF6C06 | 3 | none | 5.5 | — | 10 |
| Soy | MF-SBF6D22 | 20 | none | 11 | — | 70 |
| Soy | MF-SBF6D22 | 10 | none | 11 | — | 67 |
| Soy | MF-SBF6D22 | 3 | none | 11 | — | 13 |
| Soy | MF-SBF6C06 | 20 | Na Borohydride + 1.5 wt % Mg silicate | 5.5 | 0.42 | 71 |
| Soy | MF-SBF6C06 | 10 | Na Borohydride + 1.5 wt % Mg silicate | 5.5 | 0.42 | 42 |
| Soy | MF-SBF6C06 | 10 | Na Borohydride + 1.5 wt % Mg silicate | 5.5 | 0.42 | 60 |
| Soy | MF-SBF6C06 | 10 | Na Borohydride + 1.5 wt % Mg silicate | 5.5 | 0.42 | 70 |
| Soy | MF-SBF6C06 | 10 | Na Borohydride + 1.5 wt % Mg silicate | 5.5 | 0.42 | 69 |
| Soy | MF-SBF6C06 | 3 | Na Borohydride + 1.5 wt % Mg silicate | 5.5 | 0.42 | 61 |
| Soy | MF-SBF6C06 | 3 | Na Borohydride + 1.5 wt % Mg silicate | 5.5 | 0.42 | 67 |
| Soy | MF-SBF6C06 | 1 | Na Borohydride + 1.5 wt % Mg silicate | 5.5 | 0.42 | 42 |
| Soy | MF-SBF6D22 | 10 | Na Borohydride + 1.5 wt % Mg silicate | 11 | 0.41 | 70 |
| Soy | MF-SBF6D22 | 3 | Na Borohydride + 1.5 wt % Mg silicate | 11 | 0.41 | 65 |
| Soy | MF-SBF6D22 | 3 | Na Borohydride + 1.5 wt % Mg silicate | 11 | 0.41 | 65 |
| Soy | MF-SBF6D22 | 3 | Na Borohydride + 1.5 wt % Mg silicate | 11 | 0.41 | 48 |
| Soy | MF-SBF6D22 | 3 | Na Borohydride + 1.5 wt % Mg silicate | 11 | 0.41 | 66 |
| Soy | MF-SBF6D22 | 1 | Na Borohydride + 1.5 wt % Mg silicate | 11 | 0.41 | 23 |
| Soy | MF-SBF6D22 | 1 | Na Borohydride + 1.5 wt % Mg silicate | 11 | 0.41 | 16 |

Table 2 shows the improvements that sodium borohydride and adsorbent treatment may have on a natural oil feedstock in terms of removing catalyst poisons and improving conversion. The experimental data shows that an excessive amount of metathesis catalyst (10 to 20 ppm catalyst per mol of carbon-carbon double bonds in the feedstock, or "ppm/db") may reach the maximum theoretical conversion limit regardless of the catalyst poison level. In this example, a self-metathesis reaction of fatty acid methyl esters of soybean oil reaches an apparent maximum theoretical conversion limit of approximately 70%. As the level of metathesis catalyst is lowered below 10 ppm/db, the untreated feedstock has a lower conversion (i.e. 8-13% conversion with 3 ppm/db metathesis catalyst) (or 11-19% conversion of the maximum theoretical conversion limit). On the other hand, the feedstock treated with sodium borohydride and 1.5 wt % magnesium silicate has a much lower peroxide value (<1 meq/kg) and a much improved conversion (48-67% conversion with 3 ppm/db metathesis catalyst). This equates to approximately 69-96% of the maximum theoretical limit). This demonstrates that catalyst poisons, such as peroxides, affect the metathesis catalyst, and that removing as much of the catalyst poisons as possible may help improve conversion at lower catalyst loadings.

Example 3

This example demonstrates, among other things, the presence of non-peroxide poisons in the feedstock. Soybean oil with a low peroxide value but no chemical treatment is compared with soybean oil that was chemically treated with sodium bisulfite. The results are displayed in Table 3.

TABLE 3

| type of FAME | metathesis catalyst 827 (ppm/db) | starting material treatment | Start PV Value (meq/kg) | Final PV value (meq/kg) | GC % conversion |
|---|---|---|---|---|---|
| Soy (Cargill) | 3 | None | 0.86 | — | 12 |
| Soy (Cargill) | 3 | None | 0.86 | — | 31 |
| Soy (Cognis) | 3 | Sodium Bisulfite | 10.5 | 0.9 | 58 |
| Soy (Cognis) | 3 | Sodium Bisulfite | 10.5 | 0.9 | 67 |

As shown in Table 3, a soybean oil feedstock with a low starting peroxide value (<1 meq/kg) and no chemical treatment led to a 12-31% conversion of the feedstock (or 17-44% conversion of the maximum theoretical limit, assuming a similar 70% conversion limit to the data in Example 1) at a catalyst loading of 3 ppm/db. In comparison, a different soybean oil feedstock treated with sodium bisulfite led to a similarly diminished peroxide value, but much higher 58-67% conversion of the feedstock (or 83-96% of the maximum theoretical limit, assuming 70% conversion is the limit) with the same 3 ppm/db catalyst loading. This example shows that additional non-peroxide poisons may be present in natural oil feedstocks, and that the non-peroxides poisons may have an impact on the overall conversion. While PV is a helpful indicator, there may be other non-peroxide poisons that have not been fully quantified. This example demonstrates that chemical treatment may help diminish both peroxide and non-peroxide catalyst poisons that affect conversion.

While the present invention has been described in terms of preferred examples, it will be understood, of course, that the invention is not limited thereto since modifications may be made to those skilled in the art, particularly in light of the foregoing teachings.

What is claimed is:

1. A method of metathesizing a feedstock comprising:
   providing a feedstock comprising a natural oil;
   chemically treating the feedstock with a reducing agent under conditions sufficient to diminish catalyst poisons in the feedstock through a chemical reaction of the catalyst poisons producing a treated feedstock; and
   following chemically treating, combining a metathesis catalyst with the treated feedstock under conditions sufficient to metathesize the treated feedstock in a metathesis reaction,
   wherein the reducing agent is selected from the group consisting of bisulfites, phosphines, and thiosulfates.

2. The method of claim 1, wherein the reducing agent is added at a level of between about 0.1 wt % and about 0.9 wt % of the feedstock.

3. The method of claim 1, wherein the chemically treating is conducted at a temperature between approximately 25° C. and 90° C.

4. The method of claim 1 further comprising combining an adsorbent material with the feedstock or the treated feedstock.

5. The method of claim 4, comprising combining the adsorbent material in an amount between approximately 0.1 and 3.0 wt %.

6. The method of claim 5, comprising combining the adsorbent material in an amount between approximately 0.2 and 2.0 wt %.

7. The method of claim 1, wherein the metathesis reaction comprises a maximum theoretical conversion limit, and wherein the metathesis catalyst catalyzes the metathesis of at least 50% of the maximum theoretical conversion limit.

8. The method of claim 7, wherein the metathesis catalyst catalyzes the metathesis of at least 70% of the maximum theoretical conversion limit.

9. The method of claim 8, having a catalyst loading of approximately 5 ppm/db or less.

10. The method of claim 9, wherein the catalyst loading is approximately 2 ppm/db or less.

11. The method of claim 7, wherein the metathesis catalyst catalyzes metathesis of at least 85% conversion of the maximum theoretical conversion limit.

12. The method of claim 1, wherein the feedstock comprises a starting peroxide value of greater than 5 meq/kg and the chemically treating decreases the starting peroxide value of the feedstock to approximately 1 meq/kg or less.

13. The method of claim 12, wherein the chemically treating decreases the starting peroxide value of the feedstock to approximately 0.5 meq/kg or less.

14. The method of claim 1 comprising any two or more of the following:
   the combining comprises a catalyst loading of approximately 5 ppm/db or less, or approximately 3 ppm/db or less, or approximately 2 ppm/db or less, or approximately 1 ppm/db or less;
   the metathesis reaction comprises a maximum theoretical conversion limit and the metathesis catalyst catalyzes the metathesis of at least 50 wt %, at least 70%, or at least 85% of the maximum theoretical conversion limit;
   the chemically treating comprises treating the feedstock under conditions sufficient to diminish non-peroxide poisons in the feedstock;

the chemically treating is conducted at a temperature between approximately 25° C. and 90° C., or between approximately 50° C. and 80° C.;

the feedstock comprises a starting peroxide value of greater than 5 meq/kg, or greater than 10 meq/kg;

the chemically treating decreases the peroxide value of the feedstock to a value of approximately 1 meq/kg or less or approximately 0.5 meq/kg or less;

combining an adsorbent material to diminish the catalyst poisons within the feedstock or the treated feedstock, wherein the adsorbent material is selected from the group consisting of silica gel, bleaching clay, activated carbon, charcoal, molecular sieves, zeolites, Fuller's earth, neutral alumina, basic alumina, Celite, aluminum sulfate, calcium carbonate, Kaolin, magnesium sulfate, potassium chloride, potassium magnesium sulfate, magnesium silicate, potassium sulfate, soda ash, sodium carbonate, and sodium sulfate;

combining an adsorbent in an amount between approximately 0.1 and 3.0 wt % or between approximately 0.2 and 2.0 wt %; and the feedstock comprises one or more materials selected from the group consisting of algae oil, canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, castor oil, and natural oil derivatives of any one or more of these.

15. A method of metathesizing a feedstock comprising:
providing a feedstock comprising a natural oil;
chemically treating the feedstock with a reducing agent under conditions sufficient to diminish non-peroxide poisons in the feedstock through a chemical reaction of the non-peroxide poisons producing a treated feedstock; and
following chemically treating, combining a metathesis catalyst with the treated feedstock under conditions sufficient to metathesize the treated feedstock in a metathesis reaction,
wherein the reducing agent is selected from the group consisting of bisulfites, phosphines, and thiosulfates.

16. A method of metathesizing a feedstock comprising:
providing a feedstock comprising a natural oil having a starting peroxide value;
chemically treating the feedstock with a reducing agent for a time sufficient to reduce the starting peroxide value of the feedstock by approximately 80% or more through a chemical reaction of the peroxide poisons producing a treated feedstock;
following chemically treating, combining a metathesis catalyst with the treated feedstock under conditions sufficient to metathesize the treated feedstock in a metathesis reaction,
wherein the reducing agent is selected from the group consisting of bisulfites, phosphines, and thiosulfates.

17. The method of claim 16, wherein the treating decreases the starting peroxide value of the feedstock by approximately 90% or more.

18. A method of metathesizing a feedstock comprising:
providing a feedstock comprising a natural oil having a peroxide value of greater than 5 meq/kg;
decreasing the peroxide value to 0.5 meq/kg or less by chemically treating the feedstock with a reducing agent or a cation-inorganic base composition producing a treated feedstock;
and then, combining a metathesis catalyst with the treated feedstock under conditions sufficient to metathesize the treated feedstock in a metathesis reaction, wherein the metathesis reaction comprises a maximum theoretical conversion limit, and wherein the metathesis catalyst catalyzes the metathesis of at least 50% of the maximum theoretical conversion limit.

19. The method of claim 18, further comprising adding an adsorbent material to the feedstock or the treated feedstock.

20. The method of claim 18, having a catalyst loading of approximately 5 ppm/db or less.

21. The method of claim 20, wherein the metathesis catalyst catalyzes the metathesis of at least 70% of the maximum theoretical conversion limit.

22. The method of claim 18, having a catalyst loading of approximately is approximately 3 ppm/db or less.

23. The method of claim 22, wherein the metathesis catalyst catalyzes the metathesis of at least 70% of the maximum theoretical conversion limit.

24. The method of claim 22, wherein the metathesis catalyst catalyzes metathesis of at least 85% conversion of the maximum theoretical conversion limit.

* * * * *

UNITED STATES PATENT AND TRADEMARK OFFICE
CERTIFICATE OF CORRECTION

PATENT NO.        : 8,642,824 B2                                                                Page 1 of 1
APPLICATION NO.   : 12/672651
DATED             : February 4, 2014
INVENTOR(S)       : Lemke et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 906 days.

Signed and Sealed this
Twenty-ninth Day of September, 2015

Michelle K. Lee
*Director of the United States Patent and Trademark Office*